(12) United States Patent
Hill et al.

(10) Patent No.: US 8,252,288 B2
(45) Date of Patent: Aug. 28, 2012

(54) METHODS OF USING MULTIMERIC COMPLEXES OF ANTIGENS AND AN ADJUVANT

(75) Inventors: Fergal Hill, Saint-Beauzire (FR); Jean-Baptiste Marchand, Saint-Beauzire (FR); Laurence Dumon, Saint-Beauzire (FR)

(73) Assignee: Imaxio, Saint-Beauzire (FR)

( * ) Notice: Subject to any disclaimer, the term of this patent is extended or adjusted under 35 U.S.C. 154(b) by 0 days.

(21) Appl. No.: 13/090,707

(22) Filed: Apr. 20, 2011

(65) Prior Publication Data

US 2011/0195082 A1    Aug. 11, 2011

Related U.S. Application Data

(60) Division of application No. 12/128,687, filed on May 29, 2008, now Pat. No. 7,951,376, which is a continuation of application No. PCT/EP2006/011446, filed on Nov. 29, 2006.

(30) Foreign Application Priority Data

Nov. 30, 2005    (EP) .................................... 05292535

(51) Int. Cl.
  *A61K 39/385*    (2006.01)
  *A61K 38/02*    (2006.01)
  *C07K 14/47*    (2006.01)
  *C07K 14/435*    (2006.01)

(52) U.S. Cl. ................. 424/184.1; 424/194.1; 435/69.1; 530/351; 530/403; 536/23.5

(58) Field of Classification Search .......................... None
See application file for complete search history.

(56) References Cited

FOREIGN PATENT DOCUMENTS

| | | |
|---|---|---|
| WO | 91/11461 A1 | 8/1991 |
| WO | 2004/016283 A2 | 2/2004 |
| WO | 2004/020639 A2 | 3/2004 |
| WO | 2005/014654 A2 | 2/2005 |
| WO | WO 2005/014654 * | 2/2005 |
| WO | 2005/051414 A1 | 6/2005 |
| WO | 2005/077976 A2 | 8/2005 |

OTHER PUBLICATIONS

Office Action relating to corresponding EP Application No. 06829178.0, Sep. 29, 2010.
Ogun, et al., "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice Against Malaria," Infection and Immunity, Aug. 2008, vol. 76, No. 8, 3817-3823.
Guidry, et al., "Probing the Interface in a Human Co-Chaperonin Heptamer: Residues Disrupting Oligomeric Unfolded State Identified," BMC Biochemistry, 2003, 4:14.
Hillarp, et al., "Molecular Cloning of Rat C4b Binding Protein α- and β-Chains," The Journal of Immunology, 1997, 158: 1315-1323.
Kaidoh, et al., "Phylogeny of C4b-C3b Cleaving Activity: Similar Fragmentation Patterns of Human C4b and C3b Produced by Lower Animals," The Journal of Immunology, vol. 139, 194-201, No. 1, Jul. 1, 1987.
Kawabata, et al., "Merozoite Surface Protein 1-Specific Immune Response is Protective Against Exoerythrocytic Forms of Plasmodium Yoelii," Infection and Immunity, Nov. 2002, 6075-6082, vol. 70, No. 11.
Lintin, et al., "Derivation of the Sequence of the Signal Peptide in Human C4b-Binding Protein and Interspecies Cross-Hybridisation of the C4bp cDNA Sequence," Elsevier Science Publishers, B.V., vol. 232, No. 2, 328-332, May 1988.
Liu, et al., "High Epitope Density in a Single Recombinant Protein Molecule of the Extracellular Domain of Influenza A Virus M2 Protein Significantly Enhances Protective Immunity," Vaccine, 23 (2004) 366-371.

* cited by examiner

*Primary Examiner* — Bridget E Bunner
*Assistant Examiner* — Fozia Hamud
(74) *Attorney, Agent, or Firm* — Banner & Witcoff, Ltd.

(57) ABSTRACT

The invention relates to a product which comprises a C4bp domain of a non-mammalian origin, particularly SEQ ID NO:1, SEQ ID NO:23 or SEQ ID NO:37, or a variant thereof, and an antigen. The product is desirably in the form of a fusion protein. The chicken C4bp domain of SEQ ID NO:1 and SEQ ID NO:23 is also described. Antigens include monomeric antigens such as malarial and influenza antigens. The C4bp domain provides for assembly of multimeric complexes of the antigen, or mixtures thereof. The complexes are useful as vaccines.

14 Claims, 2 Drawing Sheets

Figure 1

```
AAG AAG CAA GGT GAT GCT GAT GTG TGC GGA GAG GTT GCT TAT ATT CAG AGC GTC GTC TCC    60
 K   K   Q   G   D   A   D   V   C   G   E   V   A   Y   I   Q   S   V   V   S    20

GAT TGC CAC GTG CCT ACA GAG GAC GTG AAA ACT CTG CTG GAG ATA CGA AAA CTC TTC CTG   120
 D   C   H   V   P   T   E   D   V   K   T   L   L   E   I   R   K   L   F   L    40

GAG ATT CAA AAA CTG AAG GTG GAA TTG CAA GGA CTG AGC AAG GAG TTC CTG GAG CAC ATT   180
 E   I   Q   K   L   K   V   E   L   Q   G   L   S   K   E   F   L   E   H   I    60

CTG CAC TGA                                                                       189
 L   H   *                                                                         62
```

Figure 2

```
CRES               656   PPNCKTFYVRKKIDQIKETFDCGLPLAELRTLLEVQKLYLEIQKLEKELGAKGGRWWP   713
Chick oligo domain   1   KKQGDADVCGEVAYIQSVVSDCHVPTEDVKTLLEIRKLFLEIQKLKVELQGLSKEFLEHILH   62
Human C4bp         492   ETPEGCEQVLTGKRLMQCLPNPEDVKMALEVYKLSLEIEQLELQRDSARQSTLDKEL   549
```

Figure 3

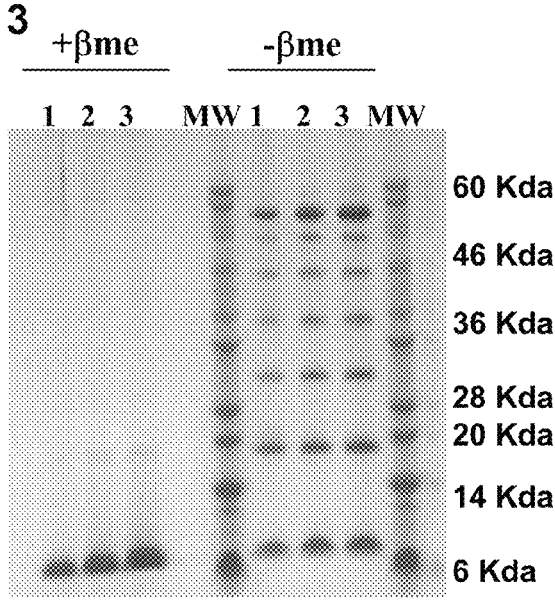

METHODS OF USING MULTIMERIC COMPLEXES OF ANTIGENS AND AN ADJUVANT

RELATED APPLICATIONS

This application is a divisional of U.S. patent application Ser. No. 12/128,687 U.S. Pat. No. 7,951,376, filed May 29, 2008, which is a continuation of PCT application no. PCT/EP2006/011446, designating the United States and filed Nov. 29, 2006; which claims the benefit of the filing date of European application no. 05292535.1, filed Nov. 30, 2005; each of which is hereby incorporated herein by reference in its entirety for all purposes.

FIELD

This invention relates to macromolecular assemblies, such as fusion proteins, comprising an adjuvant and an antigen, which assemblies provoke an enhanced immune response to the antigen in comparison to the antigen alone.

BACKGROUND

Improved methods of immunisation are needed both to improve current vaccines and to create new ones. At the same, there is a need to minimise or avoid the use of adjuvants, as only a very limited number have been approved for use in humans, and there is a widespread desire to minimise their use in animals in order to reduce animal suffering.

Recent patent applications describe the use of mammalian C4bp oligomerisation domains to increase the immunogenicity of antigens in mammals. These applications include PCT/IB2004/002717 and PCT/EP03/08926. An earlier patent, WO91/11461, discussed the use of C4bp protein fusions for immunisation but no successful immunisations were demonstrated. PCT/EP03/08928 describes methods for producing the mammalian C4bp fusion proteins. However, to date, no C4bp oligomerisation domain is known for a non-mammalian species. As there is considerable interest in vaccination of non-mammalian species, for example of birds against avian influenza, a C4bp oligomerisation domain derived from such species would be of considerable utility.

Oshiumi et al. (*J. Immunol.* 175:724-1734 (2005)) have characterised the regulator of complement activation locus in chicken and identified three proteins which they call CREM, CREG and CRES. Transcripts from each gene were characterised enabling the entire protein sequences to be deduced. One of these proteins, CRES, was described as the chicken C4bp gene.

SUMMARY

We have found a new protein sequence encoded by a DNA sequence also found in the chicken RCA locus, but distinct from any of the sequences described by Oshiumi et al. The 189 nucleotide DNA sequence and the 62 amino acid protein domain it encodes are shown in FIG. 1. We refer to this domain as the chicken C4bp oligomerisation domain.

The present invention thus provides a product which comprises: a first component of a C4bp domain of SEQ ID NO:1 or a variant thereof; and a second component of an antigen.

We have also identified an avian homologue of SEQ ID NO:1, the amino acid sequence of which is shown in SEQ ID NO:23. Therefore, in another aspect the invention provides a product which comprises a first component of a C4bp domain of SEQ ID NO:23 or a variant thereof; and a second component of an antigen.

We have also found that a CRES (complement regulatory secretory protein of chicken) domain is capable of increasing the immunogenicity of an antigen. In another aspect, therefore, the invention provides a product which comprises a first component of a C4bp domain and a second component of an antigen, wherein the C4bp domain comprises a CRES domain as shown in SEQ ID NO:37 or a variant thereof.

The first and second components may be in the form of a fusion protein. In one alternative, they may be coupled chemically, through an amino acid side chain either of the first component or through the side chain of an amino acid which has been added to the first component specifically to enable the chemical coupling of the second component.

The first and second components also may be non-covalently associated with each other. For example, the side chain of an amino acid of the first component may be modified to have an additional biotin group, and this biotin can be used to combine with streptavidin (where streptavidin is the second component) or an antigen fused to streptavidin can be combined with the first component through this biotin. In another possibility, biotinylated antigen and biotinylated first component can be held together firmly but non-covalently by adding streptavidin and purifying the complexes which result. These examples of non-covalent association are merely illustrative and those of skill in the art will understand that other types of non-covalent association, desirably leading to tight non-covalent binding of the two components, can be utilized.

For the avoidance of doubt, the designation of "first" and "second" components does not imply or indicate a specific linear order in the product of the two components. The two components may be joined in any order. Although in a preferred aspect the product will comprise the first and second components in a 1:1 ratio, it is also within the scope of the invention that more than one first component may be associated with a second component, or vice versa. For example, the ratio of a first to second component may be 1:4, 1:3, 1:2, 1:1, 2:1, 3:1 or 4:1. Where the ratio is other than 1:1 an excess of second component is preferred.

Thus where both components are polypeptides and the product is made as a fusion protein, the N- to C-terminal order of the two components may be in any permutation.

The invention further provides nucleic acid encoding a fusion protein of said first and second components. The invention also provides vectors comprising said nucleic acids and host cells carrying said vectors.

In another embodiment, the invention provides a method of making a product comprising: a first component of a C4bp domain of SEQ ID NO:1, 23, or 37, or a variant thereof; and a second component of a polypeptide antigen, the method comprising expressing nucleic acid encoding the two components in the form of a fusion protein, and recovering the product.

In another embodiment, the invention provides a method of making a product comprising: a first component of a C4bp domain of SEQ ID NO:1, 23 or 37, or a variant thereof; and a second component of polypeptide or non-polypeptide antigen, the method comprising expressing nucleic acid encoding the first component, joining said first component to the antigen, and recovering the product.

The methods of making the product may be performed in eukaryotic or prokaryotic cells.

The invention also provides a method of inducing an immune response to an antigen which method comprises administering to a subject an effective amount of a product according to the invention.

The invention also provides the product of the invention for use in a method of treatment of the human or animal body, particularly a method of inducing an immune response.

The invention further provides a pharmaceutical composition comprising a product of the invention in association with a pharmaceutically acceptable carrier or diluent.

The invention further provides a method of preparing a protective immune serum for use in passive immunization against an infectious agent, said method comprising vaccinating an animal, including a human, subject with a product of the invention, recovering antiserum from said animal, including a human. The antiserum may then be used in a method of passive immunization of subject. The subject may be a subject with, or at risk from, infection with the infectious agent.

The animal subject may particularly be a mammalian subject, including a human. An advantage of the present invention is that although the product of the invention induces antibodies against the first component in mammals (such as mice and rabbits), these antibodies do not cross-react with the endogenous mammalian C4bp protein. Thus products of the invention may be useful not only in human use but also in veterinary uses, for example in the treatment of domesticated mammals including livestock (e.g. cattle, sheep, pigs, goats, horses) and pets (e.g. cats, dogs, rodents) or in the treatment of wild mammals, such as those captive in zoos.

In another aspect, the product of the invention may be used for the treatment of non-mammalian subjects, including fowl such as chickens, turkeys, duck, geese and the like. In this aspect, the second component may include an antigen of an infectious bacterial or viral organism, such as an antigen of a *Salmonella* species, an *Escherichia* species (particularly *E. coli*), a *Campylobacter* species, an influenza virus or the like.

Further examples of antigens are discussed herein below.

DESCRIPTION OF THE DRAWINGS

FIG. 1 shows the DNA and protein sequence of the C4bp domain of the invention.

FIG. 2 shows an alignment of the C4bp domain of the invention (set forth as SEQ ID NO:1), the putative C4bp domain of CRES (set forth as SEQ ID NO:37) and human C4bp (set forth as SEQ ID NO:2).

FIG. 3 is of a gel showing a purified protein (AVD259) of the invention.

DETAILED DESCRIPTION

Figure 4:
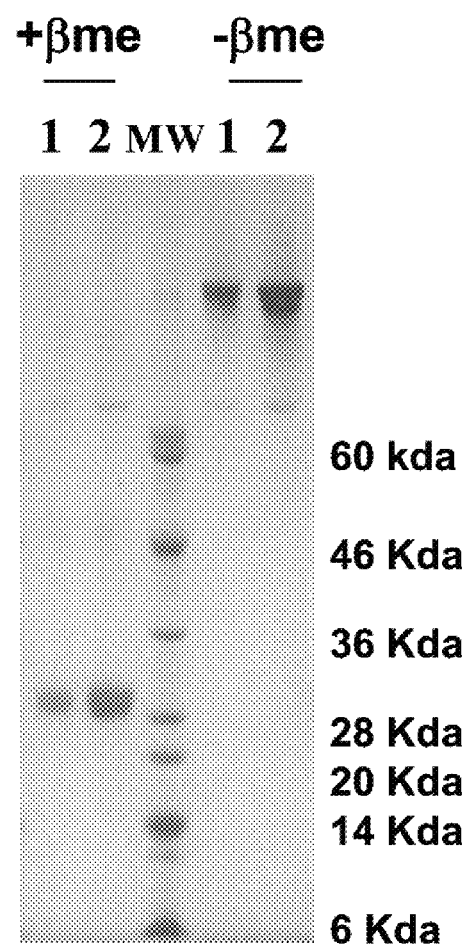
FIG. 4 shows the behaviour of AVD262 protein on an SDS-PAGE gel in the presence and absence of the reducing agent beta-mercaptoethanol (BME).

C4bp Domain of SEQ ID NO:1 or Variant Thereof

The C4bp domain of SEQ ID NO:1 comprises 62 amino acids. Variants of this protein will be capable of forming multimers. The variant will have at least 45%, more preferably at least 50%, more preferably at least 60%, more preferably at least 70%, more preferably at least 80%, even more preferably at least 90%, for example at least 95% or most preferably at least 98% sequence identity to the 62 amino acid sequence of SEQ ID NO:1.

Variants of SEQ ID NO:1 include proteins with one or more amino acid substitutions, deletions or insertions. Substitutions are particularly envisaged, as well as N- and C-terminal deletions. Thus, preferably the variant will comprise one or more of the following:

- an N-terminal deletion of from 1 to 8, such as from 1 to 4, amino acid residues;
- a C-terminal deletion of from 1 to 8, such as from 1 to 4, amino acid residues;
- from 1 to 8, such as 2, 3, 4, 5, 6 or 7 amino acid substitutions.

C4bp Domain of SEQ ID NO:23 or Variant Thereof

The C4bp domain of SEQ ID NO:23 comprises 50 amino acids.

Variants of this protein will be capable of forming multimers. The variant will have at least 45%, more preferably at least 50%, more preferably at least 60%, more preferably at least 70%, more preferably at least 80%, even more preferably at least 90%, for example at least 95% or most preferably at least 98% sequence identity to the 50 amino acid sequence of SEQ ID NO:23.

Variants of SEQ ID NO:23 include proteins with one or more amino acid substitutions, deletions or insertions. Substitutions are particularly envisaged, as well as N- and C-terminal deletions. Thus, preferably the variant will comprise one or more of the following:

- an N-terminal deletion of from 1 to 8, such as from 1 to 4, amino acid residues;
- a C-terminal deletion of from 1 to 8, such as from 1 to 4, amino acid residues;
- from 1 to 8, such as 2, 3, 4, 5, 6 or 7 amino acid substitutions.

C4bp Domain of SEQ ID NO:37 or Variant Thereof

The C4bp domain of SEQ ID NO:37 comprises 58 amino acids. This sequence represents a domain of a CRES (complement regulatory secretory protein in chicken) protein. CRES has been described by Oshiumi et al. (*J. Immunol.* 175:724-1734 (2005)) and was described as the chicken C4bp gene. Variants of the protein of SEQ ID NO:37 will be capable of forming multimers. The variant will have at least 45%, more preferably at least 50%, more preferably at least 60%, more preferably at least 70%, more preferably at least 80%, even more preferably at least 90%, for example at least 95% or most preferably at least 98% sequence identity to the 58 amino acid sequence of SEQ ID NO:37.

Variants of SEQ ID NO:37 include proteins with one or more amino acid substitutions, deletions or insertions. Substitutions are particularly envisaged, as well as N- and C-terminal deletions. Thus, preferably the variant will comprise one or more of the following:

- an N-terminal deletion of from 1 to 8, such as from 1 to 4, amino acid residues;
- a C-terminal deletion of from 1 to 8, such as from 1 to 4, amino acid residues;
- from 1 to 8, such as 2, 3, 4, 5, 6 or 7 amino acid substitutions.

Amino Acid Substitutions

Substitutions in variants of SEQ ID NO:1, 23 or 37 include conservative substitutions. Examples of conservative substitutions include those respecting the groups of similar amino acids often called the Dayhoff groups. These are as follows:

| | |
|---|---|
| Group 1 | D, E, N, Q |
| Group 2 | I, L, V, M |
| Group 3 | F, Y, W |
| Group 4 | K, R, H |
| Group 5 | S, P, T, A, G |
| Group 6 | C |

In one aspect, a variant of SEQ ID NO:1 retains some—such as at least 3, for example at least 6—or all of the following amino acid residues of SEQ ID NO:1: Cys22; Leu33; Glu34; Lys37; Leu38; Leu40; Glu41; Ile42 and Leu45.

Desirably, where some or all of these residues are present, the variant will retain the relative spacing between these residues.

The degree of sequence identity of a variant to SEQ ID NO:1, 23 or 37 may be determined by the algorithm GAP, part of the "Wisconsin package" of algorithms widely used in the art and available from Accelrys (formerly Genetics Computer Group, Madison, Wis.). GAP uses the Needleman and Wunsch algorithm to align two complete sequences in a way that maximises the number of matches and minimises the number of gaps. GAP is useful for alignment of short closely related sequences of similar length, and thus is suitable for determining if a sequence meets the identity levels mentioned above. GAP may be used with default parameters.

Examples of variants of the C4bp domain which may be made and tested for their ability to form multimers include SEQ ID NOs:5 to 14 and SEQ ID NOs 42 and 43, shown in Table 1 below:

logues of this sequence, particularly avian and reptilian homologues. As noted above, an advantage of the use of a non-mammalian protein is the avoidance of antibodies to the host's native C4bp protein. Homologues are defined as proteins with evidence of a common ancestor, i.e. likely to be the result of evolutionary divergence. Avian homologues will generally have a high degree of sequence identity to SEQ ID NO:1, 23 or 37 and such homologues, as well as their variants capable of forming multimers, may also be used in the present invention.

The means to obtain such homologues are routine techniques available to those of skill in the art. In essence, such techniques include using nucleic acid encoding SEQ ID NO:1, 23 or 37 of the present invention, or fragments thereof, as a probe to recover and to determine the sequence of C4bp homologues in other species. A wide variety of techniques are available for this, for example PCR amplification and cloning of the homologue using a suitable source of mRNA (e.g. from an embryo or an actively dividing differentiated or tumour cell), or by methods comprising obtaining a cDNA library from the animal, e.g. a cDNA library from one of the above-mentioned sources, probing said library with a nucleic acid

TABLE 1

| A | B | C |
|---|---|---|
| 1 | KKQGDADVCGEVAYIQSVVSDCHVPTEDVKTLLEIRKLFLEIQKLKVELQGLSKEFLEHILH | |
| 5 | KKQGDADVCGEVAYIQSVVSDCHVPTEDVKTLLEVRKLFLEIQKLKVELQGLSKEFLEHILH | 98 |
| 6 | KKQGDADVCGEVAYIQSVVSDCHVPTEDVKMLLEVRKLFLEIQKLKVELQGLSKEFLEHILH | 97 |
| 7 | KKQGDADVCGEVIYIQSVVSDCHVPTEDVRTLLEIRKLFLEIQKLKVELQGLSKEFLEHILH | 97 |
| 8 | KKQGDADVCGEVIYIQSVVSDCHVPTEDVKTLLEIRKLFLEIQKLKVELNGLSKEFLEHILH | 97 |
| 9 | KKQGDADVCGEVIYIQSVVSDCHVPTEDVKMLLEIRKLFLEIQKLKVELNGLSKEFLEHILH | 94 |
| 10 | KKQGDADVCGEVIYIQSVVSDCLPNTEDVKTLLEVRKLFLEIQKLKVELQGLSKEFLEHILH | 92 |
| 11 | ----DADVCGEVAYIQSVVSDCHVPTEDVKTLLEIRKLFLEIQKLKVELQGLSKEFLE---- | 87 |
| 12 | -----ADVCGEVAYIQSVVSDCHVPTEDVKTLLEIRKLFLEIQKLKVELQGLSKEF------ | 82 |
| 13 | -----ADVCGEVIYIQSVVSDCHVPTEDVKTLLEVRKLFLEIQKLKVELQGLSKEF------ | 79 |
| 14 | -----ADVCGEVAYIQSVVSDCHVPTEDVKTLLEIRKLFLEIQKLKVELNGLS--------- | 76 |
| 42 | KKQGDADVCGEVAYIQSVVSDCHVPTEDVKTLLEIRKLFLEIQKLKVELQGLSKE------- | 89 |
| 43 | KKQGDADVCGEVAYIQSVVSDCHVPTAELPTLLEIRKLFLEIQKLKVELQGLSKE------- | 82 |

A = SEQ ID NO; B = sequence, C = % identity (nearest whole number) calculated by reference to SEQ ID NO: 1.

Where deletions of the sequence are made, apart from N- or C-terminal truncations, these will preferably be limited to no more than one, two or three deletions which may be contiguous or non-contiguous.

Where insertions are made, these will also be desirably limited in number so that the size of the protein does not exceed the length of the wild type sequence by more than 20, preferably by no more than 15, more preferably by no more than 10, amino acids. Thus in the case of SEQ ID NO: 1, the protein, when modified by insertion, will desirably be no more than 82 amino acids in length.

The ability of a variant of SEQ ID NO:1, 23 or 37 to form multimers may be tested by expressing the variant in a prokaryotic host cell as illustrated in the accompanying examples, recovering the variant, and determining, e.g. by gel filtration, whether the variant forms multimers.

In an alternative aspect, variants of the C4bp domain of SEQ ID NO:1, 23 or 37 include other non-mammalian homoencoding SEQ ID NO:1, 23 or 37 under stringent conditions, and recovering a cDNA encoding all or part of the SEQ ID NO:1, 23 or 37 homologue of that animal. Where a partial cDNA is obtained, the full length coding sequence may be determined by primer extension techniques. Alternatively, where all or part of the genome sequence of the animal is available, homology searches with SEQ ID NO:1, 23 or 37 may be used to determine suitable homologues.

For example, a homologue has been identified in zebrafinch (Taeniopygio guttata) by database homology searches using SEQ ID NO:1, as set out in Example 8. The homologous amino acid sequence is shown in SEQ ID NO:23. Sequence comparison of SEQ ID NO:1 and SEQ ID NO:23 revealed an identity of 48%.

In another aspect, the invention relates to the protein of SEQ ID NO:1, 23 or 37 and their variants having at least 45%, more preferably at least 50%, more preferably at least 60%, more preferably at least 70%, more preferably at least 80%, more preferably at least 90%, more preferably at least 95%, most preferably at least 98% sequence identity capable of forming multimers as such. The invention also relates to fusion proteins of SEQ ID NO:1, 23 or 37 and a heterologous protein fused to either the N- or C-terminus. The heterologous protein may be a mammalian protein.

The protein of SEQ ID NO:1, 23 or 37 and its variants, and products of the invention may be provided in substantially isolated form, free or substantially free of material with which it is naturally associated such as other polypeptides with which it is found in the cell. The protein, its variants and products of the invention may of course be formulated with diluents or adjuvants and still for practical purposes be isolated—for example the polypeptides will normally be mixed with gelatin or other carriers if used to coat microtitre plates for use in immunoassays. The protein, its variants and products of the invention may be glycosylated, either naturally or by systems of heterologous eukaryotic cells, or they may be (for example if produced by expression in a prokaryotic cell) unglycosylated. The protein, its variants and products of the invention may optionally be phosphorylated and/or acetylated.

The protein, its variants and products of the invention may also be in a substantially purified form, in which case it will generally comprise the protein, variant or product in a preparation in which more than 90%, e.g. 95%, 98% or 99% of the protein, variant or product in the preparation is a polypeptide of the invention.

Further Features of the Product

The product of the invention may, and desirably will, comprise a flexible linker between the first and second components.

Generally such linkers are a few amino acids in length, such as from 1 to 20, e.g. from 2 to 10 amino acids in length. Such linkers are well known in the art and often consist of residues predominantly selected from glycine, serine and alanine. One such linker is a $(Gly_m-Ser)_n$ linker, where m and n are each independently from 1 to 4. These are used in the art to attach protein domains to each other. Thus the first component may be linked to the second by such a linker.

It is preferred that when the first component is the C4bp domain and the product is in the form of a fusion protein, it is at the C-terminal of the product.

Where the C4bp domain is at the N-terminal of the product (or the antigen is not expressed in the form of a fusion with the C4bp), it will be necessary to incorporate a sequence of amino acids suitable for expression of the protein. This will include at least an N-terminal methionine. For bacterial expression, the second amino acid (after Met) is desirably alanine. The N-terminal sequence may include a cleavage site for chemical or enzymatic removal of all or part of the sequence. For products of the invention in which the antigen is C-terminal to the first component, such an N-terminal region is desirably no more than 20, such as no more than 10, amino acids.

Antigen

An antigen is any molecule capable of being recognized by an antibody or T-cell receptor. However, not all antigens are immunogens. An immunogen is any substance which elicits an immune response. In one aspect, the present invention enables antigens which are not immunogens to become immunogens, and those antigens which are weak immunogens to become better immunogens.

An important characteristic of the present invention is that monomeric antigens are highly preferred when antigens are produced by being genetically fused to the C4bp because they do not impede the assembly of the C4bp domain into an oligomeric and therefore functional form.

However in an alternative aspect, the antigens may be non-monomeric. This may be particularly when they are coupled chemically or non-covalently to the C4bp domain.

A monomeric antigen may thus fall into two main groups:

1) An antigen which is a fragment or variant of a parent protein which in its natural state is multimeric (i.e. dimeric or a higher order multimer), but which antigen itself does not form multimers under conditions in which the parent protein does form such multimers; and
2) An antigen which in its natural state is a monomer.

Examples of both types of antigen are discussed further herein below.

Monomeric antigens have in common that they can be encoded on a single piece of DNA and when this DNA is fused to DNA encoding a C4bp domain and subsequently translated into protein, the antigen is linked through a unique point on the antigen to a single C4bp domain chain. A simple example of such an antigen would be lysozyme from hen egg white. The cDNA encoding the full-length lysozyme open reading frame can be fused to the C4bp open reading frame in such a manner that the assembly of the C4bp part of the resulting fusion protein is not impeded.

After biosynthesis, a single polypeptide chain fused to a C4bp may be processed, for example by proteases, thus generating new N- and C-termini within the polypeptide chain. If the two or more chains generated by proteolytic cleavage remain attached to one another through, for example, disulphide bonds, the C4bp fusion protein will, at the end of processing have attached to it a protein which would normally not be considered monomeric. However, for the purposes of this invention, proteins of this type are considered monomeric because they are encoded as a single fusion protein in a single open reading frame. An example of this type would be proinsulin, which is processed after biosynthesis to have two chains, called A and B, which are linked by disulphide bonds. A fragment of proinsulin, called the C peptide, is removed following proteolytic processing of the precursor fusion protein.

The monomeric antigen may be derived from a protein which is not necessarily monomeric in its natural state. Thus many antigens found in a polymeric state in nature can be modified, for example by protein engineering techniques, so that they become monomeric. There are three examples. An example of such an antigen is one derived from the influenza virus hemagglutinin protein. This is well known to form a complex trimeric structure in its natural state (Wilson et al. *Nature* 289:366-373 (1981)). However, it is possible, by removing the coiled coil responsible for trimerizing the molecule to obtain a monomeric fragment. A specific example is provided by the work of Jeon and Arnon (*Viral Immunology* 15:165-176 (2002)). These authors used only residues 96-261 of the hemagglutinin in order to have a fragment encompassing only the globular region of the hemagglutinin.

Another example is the *Plasmodium merozoite* surface protein 1 (MSP1). This large (approximately 200 kDa) protein decorates the surface of merozoites which are responsible for the blood stage of malaria infections. It is normally fixed to the surface of merozoites through a C-terminal GPI anchor (where GPI is glycosylphosphatidylinisotol). This GPI anchor is preceded by a hydrophobic stretch of amino acids. As a consequence of this anchor, neither the full-length MSP1, nor the C-terminal fragment called MSP1.19 (which remains membrane-bound even as the merozoite invades erythrocytes) is ever found in a monomeric state in nature. The same applies to many membrane proteins which have a single hydrophobic transmembrane region. The present invention is best practised by deleting these hydrophobic stretches. See the example below which describes the fusion of MSP1.19 proteins to C4bp domains.

Thus in one preferred aspect of the invention, the product of the invention is a fusion of a plasmodium MSP1 monomeric antigenic fragment fused to a C4bp domain. The plasmodium MSP1 antigenic fragment may comprise from about 50 to about 200, preferably from about 50 to about 150, amino acids. The antigenic fragment may be from any *plasmodium* species, such as *Plasmodium falciparum* or *Plasmodium vivax* or *Plasmodium ovale* or *Plasmodium malariae* (all of which are capable of causing illness in humans) or *Plasmodium yoelii.*

Although deletions are the easiest method of rendering monomeric otherwise oligomeric proteins, in some cases, mutating one or more amino acids may suffice. An example of this is the Cpn10 protein, which in its natural state is a heptameric protein, like the C4bp in its principal isoforms. The mutation of a single amino acid in Cpn10 converts it into a monomeric mutant which makes it suitable for fusion to a C4bp domain (Guidry et al. *BMC Biochemistry* 4:14-26 (2003)). An alternative approach to monomerize this protein was to delete N-terminal or C-terminal amino acids (Llorca et al. *Biochem. Biophysica Acta* 1337:47-56 (1997); Seale and Horowitz, *J. Biol. Chem.* 270:30268-30270 (1995)) and thereby the regions responsible for inter-subunit interaction.

In general, for protein that will have a strong propensity to assemble into oligomeric structures (such as viral capsid proteins) thus disrupting the assembly of a C4bp domain to which it is fused, the principles of deleting the regions responsible for protein-protein interaction or of mutating residues at the interface can be applied to obtain monomeric proteins.

Antigens can be classified into two categories, both of which are suitable for use with the invention. The first category is exogenous antigens, and includes all molecules found in infectious organisms. Bacterial immunogens, parasitic immunogens and viral immunogens are useful as polypeptide moieties to create multimeric or hetero-multimeric C4bp fusion proteins useful as vaccines.

Bacterial sources of these immunogens include those responsible for bacterial pneumonia, meningitis, cholera, diphtheria, pertussis, tetanus, tuberculosis and leprosy.

Parasitic sources include malarial parasites, such as *Plasmodium*, as well as *trypanosomal* and *leishmania* species.

Viral sources include poxviruses, e.g., smallpox virus, cowpox virus and orf virus; herpes viruses, e.g., herpes simplex virus type 1 and 2, B-virus, varicella zoster virus, cytomegalovirus, and Epstein-Barr virus; adenoviruses, e.g., mastadenovirus; papovaviruses, e.g., papillomaviruses such as HPV16, and polyomaviruses such as BK and JC virus; parvoviruses, e.g., adeno-associated virus; reoviruses, e.g., reoviruses 1, 2 and 3; orbiviruses, e.g., Colorado tick fever; rotaviruses, e.g., human rotaviruses; alphaviruses, e.g., Eastern encephalitis virus and Venezuelan encephalitis virus; rubiviruses, e.g., rubella; flaviviruses, e.g., yellow fever virus, Dengue fever viruses, Japanese encephalitis virus, Tick-borne encephalitis virus and hepatitis C virus; coronaviruses, e.g., human coronaviruses; paramyxoviruses, e.g., parainfluenza 1, 2, 3 and 4 and mumps; morbilliviruses, e.g., measles virus; pneumovirus, e.g., respiratory syncytial virus; vesiculoviruses, e.g., vesicular stomatitis virus; lyssaviruses, e.g., rabies virus; orthomyxoviruses, e.g., influenza A and B; bunyaviruses e.g., LaCrosse virus; phleboviruses, e.g., Rift Valley fever virus; nairoviruses, e.g., Congo hemorrhagic fever virus; hepadnaviridae, e.g., hepatitis B; arenaviruses, e.g., 1 cm virus, Lasso virus and Junin virus; retroviruses, e.g., HTLV I, HTLV II, HIV-1 and HIV-2; enteroviruses, e.g., polio virus 1,-2 and 3, coxsackie viruses, echoviruses, human enteroviruses, hepatitis A virus, hepatitis E virus, and Norwalk-virus; *rhinoviruses* e.g., human *rhinovirus*; and filoviridae, e.g., Marburg (disease) virus and Ebola virus.

Antigens from these bacterial, viral and parasitic sources may be used in the production of multimeric proteins useful as vaccines. The multimers may comprise a mixture of monomers carrying different antigens.

Antigens from these bacterial, viral and parasitic sources can be considered as exogenous antigens because they are not normally present in the host and are not encoded in the host genome. Endogenous antigens, in contrast, are normally present in the host or are encoded in the host genome, or both. The ability to generate an immune response to an endogenous antigen is useful in treating tumours that bear that antigen, or in neutralising growth factors for the tumour. An example of the first type of endogenous antigen is HER2, the target for the monoclonal antibody called Herceptin. An example of the second, growth factor, type of endogenous antigen is gonadotrophin releasing hormone (called GnRH) which has a trophic effect on some carcinomas of the prostate gland.

Products of the present invention may therefore be used, alone or in combination with other anti-tumor treatment, e.g. chemotherapy, for the treatment or prevention of cancer.

Treatment may, for example, cause a reduction in the rate or amount of growth of a tumor. Treatment also includes reducing or ameliorating the undesirable symptoms of cancer. Current anti-tumor treatments include e.g. chemotherapy (CT), radiation therapy (RT) and surgery, and combinations thereof, as well as specialized treatments such as use of angiogenesis inhibitors, biological therapies, including adjuvant therapy to boost the patient's immune system, antibody therapy, vaccine therapy, and photodynamic therapy.

"Chemotherapy" (CT) refers to treatment with anti-cancer drugs. The term encompasses numerous classes of agents including platinum-based drugs, alkylating agents, anti-metabolites, anti-miotic agents, anti-microtubule agents, plant alkaloids, and anti-tumor antibiotics, kinase inhibitors, proetasome inhibitors, EGFR inhibitors, HER dimerization inhibitors, VEGF inhibitors, and antisense molecules, and includes antibodies. Such drugs include but are not limited to adriamycin, melphalan, ara-C, BiCNU, busulfan, CCNU, pentostatin, the platinum-based drugs carboplatin, cisplatin and oxaliplatin, cyclophosphamide, daunorubicin, epirubicin, dacarbazine, 5-fluorouracil (5-FU), fludarabine, hydroxyurea, idarubicin, ifosfamide, methotrexate, altretamine, mithramycin, mitomycin, bleomycin, chlorambucil, mitoxantrone, nitrogen mustard, mercaptopurine, mitozantrone, paclitaxel(Taxol®), vinblastine, vincristine, vindesine, etoposide, gemcitabine, monoclonal antibodies such as Herceptin®, Rituxan®, Campath®, Zevelin® and Bexxar®, irinotecan, leustatin, vinorelbine, STI-571(Gleevac®), tamoxifen, docetaxel, topotecan, capecetabine (Xeloda®), raltitrexed, streptozocin, tegafur with uracil, temozolomide, thioguanine, thiotepa, podophyllotoxin, filgristim, profimer sodium, letrozole, amifostine, anastrozole, temozolomide, arsenic trioxide, epithalones A and B tretinioin, interleukins (e.g. 2 and 12) and interferons, e.g., alpha and gamma, bortezomib, huBrE3, Genasense, Ganite, FIT-3 ligand, MLN491RL, MLN2704, MLN576, and MLN518. Antiangiogenic agents include but are not limited to BMS-275291, Dalteparin(Fragmin®) 2- methoxyestradiol (2-ME), thalodmide, CC-5013 (thalidomide analog), maspin, combretastatin A4 phosphate, LY317615, soy isoflavone (genistein; soy protein isolate), AE-941(Neovastat™; GW786034), anti-VEGF antibody (Bevacizumab; Avastin™), PTK787/ZK 222584, VEGFtrap, ZD6474, EMD 121974, anti-anb3 integrin antibody (Medi-522; Vitaxin™), carboxyamidotriazole(CAI), celecoxib (Celebrex®), halofuginone hydrobromide (Tempostatin™), and Rofecoxib (VIOXX®).

The term "chemotherapy" also includes gene therapy with agents such as interferon and the interleukins, i.e., administration of a vector encoding genes for the interferons or interleukins. See e.g., Heller et al., *Technol. Cancer Res. Treat.* 1(3):205-209 (2002).

Immunogens made using the present invention may be used for research or therapeutic purposes. For example, research applications include the generation of antisera to predicted gene products in genome sequence data. This requirement applies to prokaryotic, such as bacterial, and eukaryotic, including fungal and mammalian, gene products. The antigen may be any size conventional in the art for vaccines, ranging from short peptides to very large proteins.

Non-polypeptide immunogens may be, for example, carbohydrates or nucleic acids. The polysaccharide coats of *Neisseria* species or of *Streptococcus pneumoniae* species are examples of carbohydrates which may be used for the purposes of the invention.

Where a non-polypeptide immunogen is part of the product of the invention, the immunogen may be covalently attached to the first component of the product using routine synthetic methods. Generally, the immunogen may be attached to either the N- or C-terminal of a C4bp domain or variant thereof comprising the first component, or to an amino acid side chain group (for example the epsilon-amino group of lysine or the thiol group of cysteine), or a combination thereof. More than one immunogen per fusion protein may be added. To facilitate the coupling, a cysteine residue may be added to the C4bp domain or variant thereof, for example as the N- or C-terminus.

The present invention has many advantages in the generation of an immune response. For example, the use of multimers can permit the presentation of a number of antigens, simultaneously, to the immune system. This allows the preparation of polyvalent vaccines, capable of raising an immune response to more than one epitope, which may be present on a single organism or a number of different organisms.

Accordingly, in a further aspect the monomeric antigen may be a synthetic antigen comprising two different epitopes, either from two different organisms or from two different proteins of the same organism. An example of the latter is a fusion of a sporozoite antigen sequence, e.g. two or more NANP repeat sequences from the circumsporozoite protein joined to an MSP1 sequence. A second example of the latter is a fusion of the M2e sequence described by Neirynck et al. (*Nature Medicine* 5:1157-1163 (1999)) fused to a monomeric influenza hemagglutinin fragment.

Thus, vaccines formed according to the invention may be used for simultaneous vaccination against more than one disease, or to target simultaneously a plurality of epitopes on a given pathogen. The epitopes may be present in single monomer units or on different monomer units which are combined to provide a heteromultimer.

Nucleic Acids

The C4bp domains and products of the invention comprising such domains (in both cases including variants thereof) may be produced by expression of a fusion protein in a prokaryotic or eukaryotic host cell, using a nucleic acid construct encoding the protein. Where the antigen is a polypeptide, the expression of the fusion protein from a nucleic acid sequence can be used to produce a product of the invention.

Thus the invention provides a nucleic acid construct, generally DNA or RNA, which encodes a protein of the invention.

The construct will generally be in the form of a replicable vector, in which sequence encoding the protein is operably linked to a promoter suitable for expression of the protein in a desired host cell.

The vectors may be provided with an origin of replication and optionally a regulator of the promoter. The vectors may contain one or more selectable marker genes. There are a wide variety of prokaryotic and eukaryotic expression vectors known as such in the art, and the present invention may utilise any vector according to the individual preferences of those of skill in the art.

A wide variety of prokaryotic host cells can be used in the method of the present invention. These hosts may include strains of *Escherichia, Pseudomonas, Bacillus, Lactobacillus, Thermophilus, Salmonella, Enterobacteriacae* or *Streptomyces*. For example, if *E. coli* from the genera *Escherichia* is used in the method of the invention, preferred strains of this bacterium to use would include derivatives of BL21(DE3) including C41(DE3), C43(DE3) or CO214(DE3), as described and made available in WO98/02559.

Even more preferably, derivatives of these strains lacking the prophage DE3 may be used when the promoter is not the T7 promoter.

Prokaryotic vectors includes vectors bacterial plasmids, e.g., plasmids derived from *E. coli* including ColEI, pCR1, pBR322, pMB9 and their derivatives, wider host range plasmids, e.g., RP4; phage DNAs, e.g., the numerous derivatives of phage lambda, e.g., NM989, and other DNA phages, e.g., M13 and filamentous single stranded DNA phages. These and other vectors may be manipulated using standard recombinant DNA methodology to introduce a nucleic acid of the invention operably linked to a promoter.

The promoter may be an inducible promoter. Suitable promoters include the T7 promoter, the tac promoter, the trp promoter, the lambda promoters $P_L$ or $P_R$ and others well known to those skilled in the art.

A wide variety of eukaryotic host cells may also be used, including for example yeast, insect and mammalian cells. Mammalian cells include CHO and mouse cells, African green monkey cells, such as COS-1, and human cells.

Many eukaryotic vectors suitable for expression of proteins are known. These vectors may be designed to be chromosomally incorporated into a eukaryotic cell genome or to be maintained extrachromosomally, or to be maintained only transiently in eukaryotic cells. The nucleic acid may be operably linked to a suitable promoter, such as a strong viral promoter including a CMV promoter, and SV40 T-antigen promoter or a retroviral LTR.

To obtain a product of the invention, host cells carrying a vector of the invention may be cultured under conditions suitable for expression of the protein, and the protein recovered from the cells of the culture medium.

Cell Culturing

Plasmids encoding fusion proteins in accordance with the invention may be introduced into the host cells using conventional transformation techniques, and the cells cultured under conditions to facilitate the production of the fusion protein. Where an inducible promoter is used, the cells may initially be cultured in the absence of the inducer, which may then be added once the cells are growing at a higher density in order to maximise recovery of protein.

Cell culture conditions are widely known in the art and may be used in accordance with procedures known as such.

Although WO91/11461 suggests that prokaryotic host cells may be used in the production of C4bp-based proteins, there was no experimental demonstration of such production.

Recently, it has been found that proteins fused to the C4bp produced in the prokaryotic expression systems retain their functional activity. This is disclosed in WO2004/020639, the contents of which are incorporated herein by reference. Such methods may be used in the production of fusion proteins of the present invention.

Recovery of Protein from Culture

Once the cells have been grown to allow for production of the protein, the protein may be recovered from the cells. Because we have found that surprisingly, the protein remains soluble, the cells will usually be spun down and lysed by sonication, for example, which keeps the protein fraction soluble and allows this fraction to remain in the supernatant following a further higher speed (e.g. 15,000 rpm for 1 hour) centrifugation.

We have also surprisingly found that truncation and/or variation of the C4bp domain may affect the solubility of the fusion protein. Truncation may be at the C- or N-terminus. In particular, a C-terminal truncation may improve solubility of the fusion protein. For example, example 11 shows that deletion of the last seven C-terminal amino acids of the C4bp domain as shown in SEQ ID NO:1 improves solubility of the fusion protein.

The fusion protein in the supernatant protein fraction may be purified further by any suitable combination of standard protein chromatography techniques. We have used ion-exchange chromatography, gel filtration chromatography and affinity chromatography.

Depending on the intended uses of the protein, the protein may be subjected to further purification steps, for example dialysis, or to concentration steps, for example freeze drying.

It has been found that the C-terminus of the C4bp domain as shown in SEQ ID NO:1 (or variant thereof) facilitates purification of the fusion protein. In particular it has been found that the C-terminus may improve binding of a fusion protein to a purification matrix such as a purification column, e.g. a nickel affinity chromatography column. For example, it has been shown in example 11 that the last seven C-terminal amino acids of the C4bp domain of SEQ ID NO:1 (FLEHILH) facilitate binding of a fusion protein to a nickel affinity column.

The last seven C-terminal amino acids comprise only two histidines. While it is known that the widely used hexa histidine tags (also called polyhistidine tag), which comprise six consecutive histidines, show a high affinity to nickel columns, we show -we believe for the first time- that two histidines are sufficient to enable binding. The two histidines may further be spaced apart by a number of intervening amino acids. There may be one, two or more intervening amino acids.

It can therefore be envisaged that the C-terminus of SEQ ID NO:1, or a variant thereof, may be used as a purification tag. It may be attached to another protein, e.g. by fusion, to facilitate purification of said protein. It may be attached at any position of a protein. It may be attached at the N- or at the C-terminus. In particular, the sequence FLEHILH (SEQ ID NO:44) or a variant thereof could be used as a purification tag for other proteins.

Variants of FLEHILH include polypeptides with one or more amino acid substitutions, deletions or insertions. Variants are capable of binding to a nickel affinity chromatography column. A variant may have two histidines spaced apart by one, two, three, four or more intervening amino acids.

Compositions and Uses Thereof

Proteins and products according to the invention may be prepared in the form of a pharmaceutical composition. The product will be present with one or more pharmaceutically acceptable carriers or diluents. The composition will be prepared according to the intended use and route of administration of the product. Thus the invention provides a composition comprising a product of the invention in multimeric form together with one or more pharmaceutically acceptable carriers or diluents, and the use of such a composition in methods of immunotherapy for treatment or prophylaxis of a human or animal subject.

Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy.

Liquid pharmaceutically administrable compositions can, for example, be prepared by dissolving, dispersing, etc, a fusion protein of the invention with optional pharmaceutical adjuvants in a carrier, such as, for example, water, saline aqueous dextrose, glycerol, ethanol, and the like, to thereby form a solution or suspension. If desired, the composition to be administered may also auxiliary substances such as pH buffering agents and the like. Actual methods of preparing such dosage forms are known, or will be apparent, to those skilled in this art; for example, see *Remington's Pharmaceutical Sciences*, Mack Publishing Company, Easton, Pa., 19th Edition, 1995.

Compositions according to the invention may additionally comprise one or more adjuvants, for example mineral salts such as aluminium hydroxide or calcium phosphate, or cytokines such as IL-12 or GM-CSF. A fuller list of suitable adjuvants is given in Table 1 of Singh and O'Hagan, *Nature Biotechnology*, 17:1075-1081 (1999), the disclosure of which is incorporated herein by reference.

Products according to the invention, desirably in the form of a composition or formulation may be used in methods of treatment as described herein, by administration of the product or composition thereof to a human or animal subject. The amount effective to alleviate the symptoms of the subject being treated will be determined by the physician taking into account the patient and the condition to be treated. Dosage forms or compositions containing active ingredient in the range of 0.25 to 95% with the balance made up from non-toxic carrier may be prepared.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. A more recently devised approach for parenteral administration employs the implantation of a slow-release or sustained-release system, such that a constant level of dosage is maintained. See, e.g., U.S. Pat. No. 3,710,795.

Doses of the product will be dependent upon the nature of the antigen and may be determined according to current practice for administration of that antigen in conventional vaccine formulations.

Passive Immunisation

In a further aspect, the invention provides a means for passive immunisation of a subject with an immune serum containing antibodies obtained by vaccination of a host subject with a product of the invention. The host subject may be a human or non-human mammal. Thus in a further aspect, the invention provides an immune serum obtained by such a method, and the use of such an immune serum in a method of treatment of the human or animal body.

DNA Vaccines

In another aspect, the invention provides a eukaryotic expression vector comprising a nucleic acid sequence encoding a recombinant fusion protein product of the invention for use in the treatment of the human or animal body.

Such treatment would achieve its therapeutic effect by introduction of a nucleic acid sequence encoding an antigen for the purposes of raising an immune response. Delivery of nucleic acids can be achieved using a plasmid vector (in "naked" or formulated form) or a recombinant expression vector. For a review of DNA vaccination, see Ada G. and Ramshaw I, in *Expert Opinion in Emerging Drugs* 8:27-35, (2003).

Various viral vectors which can be utilized for gene delivery include adenovirus, herpes virus, vaccinia or an RNA virus such as a retrovirus. The retroviral vector may be a derivative of a murine or avian retrovirus. Examples of retroviral vectors in which a single foreign gene can be inserted include, but are not limited to: Moloney murine leukaemia virus (MoMuLV), Harvey murine sarcoma virus (HaMuSV), murine mammary tumour virus (MuMTV), and Rous Sarcoma Virus (RSV). When the subject is a human, a vector such as the gibbon ape leukaemia virus (GaLV) can be utilized.

The vector will include a transcriptional regulatory sequence, particularly a promoter region sufficient to direct the initiation of RNA synthesis. Suitable eukaryotic promoters include the promoter of the mouse metallothionein I gene (Hamer et al., *J. Molec. Appl. Genet.* 1:273 (1982)); the TK promoter of Herpes virus (McKnight, *Cell* 31:355 (1982)); the SV40 early promoter (Benoist et al., *Nature* 290:304 (1981)); the Rous sarcoma virus promoter (Gorman et al., *Proc. Natl. Acad. Sci. USA* 79:6777 (1982)); and the cytomegalovirus promoter (Foecking et al., *Gene* 45:101 (1980)).

Administration of vectors of this aspect of the invention to a subject, either as a plasmid vector or as part of a viral vector can be affected by many different routes. Plasmid DNA can be "naked" or formulated with cationic and neutral lipids (liposomes) or microencapsulated for either direct or indirect delivery. The DNA sequences can also be contained within a viral (e.g., adenoviral, retroviral, herpesvirus, pox virus) vector, which can be used for either direct or indirect delivery. Delivery routes include but are not limited to oral, intramuscular, intradermal (Sato, Y. et al., *Science* 273:352-354 (1996)), intravenous, intra-arterial, intrathecal, intrahepatic, inhalation, intravaginal instillation (Bagarazzi et al., *J. Med. Primatol.* 26:27 (1997)), intrarectal, intratumour or intraperitoneal.

Thus the invention includes a vector as described herein as a pharmaceutical composition useful for allowing transfection of some cells with the DNA vector such that a therapeutic polypeptide will be expressed and have a therapeutic effect, namely to induce an immune response to an antigen. The pharmaceutical compositions according to the invention are prepared by bringing the construct according to the present invention into a form suitable for administration to a subject using solvents, carriers, delivery systems, excipients, and additives or auxiliaries. Frequently used solvents include sterile water and saline (buffered or not). One carrier includes gold particles, which are delivered biolistically (i.e., under gas pressure). Other frequently used carriers or delivery systems include cationic liposomes, cochleates and microcapsules, which may be given as a liquid solution, enclosed within a delivery capsule or incorporated into food.

An alternative formulation for the administration of gene delivery vectors involves liposomes. Liposome encapsulation provides an alternative formulation for the administration of polynucleotides and expression vectors. Liposomes are microscopic vesicles that consist of one or more lipid bilayers surrounding aqueous compartments. See, generally, Bakker-Woudenberg et al., *Eur. J. Clin. Microbiol. Infect. Dis.* 12(Suppl. 1):S61 (1993), and Kim, *Drugs* 46:618 (1993). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µM to greater than 10 µM. See, for example, Machy et al., *Liposomes in Cell Biology and Pharmacology* (John Libbey) (1987); and Ostro et al., *American J. Hosp. Phann.* 46:1576 (1989).

Expression vectors can be encapsulated within liposomes using standard techniques. A variety of different liposome compositions and methods for synthesis are known to those of skill in the art. See, for example, U.S. Pat. No. 4,844,904, U.S. Pat. No. 5,000,959, U.S. Pat. No. 4,863,740, U.S. Pat. No. 5,589,466, U.S. Pat. No. 5,580,859, and U.S. Pat. No. 4,975,282, all of which are hereby incorporated by reference.

In general, the dosage of administered liposome-encapsulated vectors will vary depending upon such factors as the patient's age, weight, height, sex, general medical condition and previous medical history. Dose ranges for particular formulations can be determined by using a suitable animal model.

The invention is illustrated by the following examples.

EXAMPLE 1

Cloning and Expression of the Chicken C4bp Oligomerisation Domain

The DNA fragment encoding the chicken C4bp oligomerisation domain was amplified from chicken genomic DNA using the following oligonucleotide primers (restriction sites are underlined):

```
oAVD469:
                                            (SEQ ID NO: 15)
5' GGGGGGATCCAAGAAGCAAGGTGATGCTGATGTGTGCGG 3'
and oAVD470:
                                            (SEQ ID NO: 16)
5' GGGGGAATTCTTATTAGTGCAGAATGTGCTCCAGGAACTC 3'
``` and cloned, as a BamHI/EcoRI fragment downstream of a translation enhancer sequence and the T7 promoter in a plasmid vector, thus creating the plasmid pAVD259. SEQ ID NO:17 shows the sequence of the protein, AVD259, expressed from this plasmid and SEQ ID NO:18 shows the nucleotide sequence encoding it:

```
SEQ ID NO: 17: the AVD259 protein
MALKKHHENE ISHHGSKKQG DADVCGEVAY IQSVVSDCHV

PTEDVKTLLE IRKLFLEIQK LKVELQGLSK EFLEHILH
```

-continued

```
SEQ ID NO: 18: DNA sequence encoding the AVD259
protein
ATGGCCTTGAAGAAACACCATGAAAATGAGATCTCTCATCATGGATCCAA

GAAGCAAGGTGATGCTGATGTGTGCGGAGAGGTTGCTTATATTCAGAGCG

TCGTCTCCGATTGCCACGTGCCTACAGAGGACGTGAAAACTCTGCTGGAA

ATACGAAAACTCTTCCTGGAGATTCAAAAACTGAAGGTGGAATTGCAAGG

ACTGAGCAAGGAGTTCCTGGAGCACATTCTGCACTAA
```

EXAMPLE 2

Purification and Characterisation of the AVD259 Protein

Expression

The plasmid pAVD259 encoding the chicken C4bp oligomerisation domain was expressed in the *E. coli* strain C41 (DE3). The transformed cells were grown in LB medium at 37° C. to an OD600 of approximately 0.6, then expression was induced with IPTG at a final concentration of 0.5 mM, and the culture was grown for a further four hours at 37° C. at which point the cells were harvested by centrifugation.

Purification of AVD259 Protein The protein AVD259 was purified from 1 liter of C41(DE3) cells. All of the protein was found in the soluble fraction after the cells were lysed by sonication in a buffer containing 20 mM Tris pH8.0. The supernatant after centrifugation was loaded on a Nickel affinity column.

Affinity Column Purification

The column was equilibrated in 20 mM Tris pH 8.0 (buffer A). The protein was eluted with Buffer B (buffer A plus 300 mM NaCl and 300 mM Imidazole).

Gel Filtration Column (Superdex 200 26/60 Prep Grade)

A Superdex 200 26/60 column was equilibrated with 20 mM Tris buffer pH8, and the concentrated AVD259 protein from the affinity column was loaded. The protein eluted in a volume of 200 mls.

Biophysical Characterisation

The oligomeric state of C4bp oligomerisation domain fusion proteins can be checked easily by comparing the behaviour of the protein on an SDS-PAGE gel in the presence and absence of the reducing agent beta-mercaptoethanol (BME).

FIG. 3 shows the behaviour of freshly purified AVD259 protein; the protein was rapidly purified (in less than 48 hours) and so the formation of disulphide bonds, which occurs spontaneously on exposure to air, is incomplete. (The disulphide bonds can not form in the reducing environment of the bacterial cytosol). Each lane 1 contains 3pg, each lane 2 contains 5 μg and each lane 3 contains 8 μg. In the presence of beta-mercaptoethanol (labelled +βme) the protein runs exclusively as a monomer, with an apparent size of approximately 8 kDa. In the absence of beta-mercaptoethanol (labelled −βme), the monomer, dimer, trimer, tetramer, pentamer, hexamer and heptamer bands can be clearly seen.

EXAMPLE 3

Expression of the *Plasmodium Yoelii* MSP1.19-Chicken C4bp Fusion Protein (AVD262)

To determine the effect of fusing the chicken C4bp oligomerisation domain to an antigen, the MSP1.19 antigen from *Plasmodium yoelii* was fused to it. This was achieved by replacing the BamHI-EcoRI fragment encoding murine C4bp in the plasmid pAVD108 by the BamHI-EcoRI fragment from pAVD259 (described in Example 1), thus creating the plasmid pAVD262. The plasmid pAVD108 has been described previously in Example 4 of PCT/IB2004/002717. The fusion protein, called AVD262, was expressed in, and purified from the bacterial strain C41(DE3). The purified fusion protein was used to immunise mice, rabbits and chickens without the addition of any adjuvant.

The nucleotide sequence encoding the AVD262 fusion protein is SEQ ID NO:19 as follows:

```
atgagatctcacattgcctctattgctttgaacaacttgaacaagtctgg tttggtaggagaaggtgagtctaagaagattttggctaagatgctgaaca tggacggtatggacttgttgggtgttgaccctaagcatgtttgtgttgac actagagacattcctaagaacgctggatgtttcagagacgacaacggtac tgaagagtggagatgtttgttgggttacaagaagggtgagggtaacacct gcgttgagaacaacaaccctacttgcgacatcaacaacggtggatgtgac ccaaccgcctcttgtcaaaacgctgaatctaccgaaaactccaagaagat tatttgcacctgtaaggaaccaacccctaacgcctactacgagggtgttt tctgttcttcttccGGATCCAAGAAGCAAGGTGATGCTGATGTGTGCGGA

GAGGTTGCTTATATTCAGAGCGTCGTCTCCGATTGCCACGTGCCTACAGA

GGACGTGAAAACTCTGCTGGAAATACGAAAACTCTTCCTGGAGATTCAAA

AACTGAAGGTGGAATTGCAAGGACTGAGCAAGGAGTTCCTGGAGCACATT

CTGCACTAA
```

The amino acid sequence of the fusion protein AVD262 encoded by this construct is SEQ ID NO:20 as follows:

```
MRSHIASIAL NNLNKSGLVG EGESKKILAK MLNMDGMDLL

GVDPKHVCVD TRDIPKNAGC FRDDNGTEEW RCLLGYKKGE

GNTCVENNNP TCDINNGGCD PTASCQNAES TENSKKIICT

CKEPTPNAYY EGVFCSSSGS KKQGDADVCG EVAYIQSVVS

DCHVPTEDVK TLLEIRKLFL EIQKLKVELQ GLSKEFLEHI LH
```

Residues 4-138 of this sequence correspond to residues 1619-1753 of *Plasmodium yoelii* MSP1, and residues 141-202 of this sequence correspond to the 62 residues of the chicken C4bp oligomerisation domain. A GS linker sequence appears between the two components.

Expression

The plasmid pAVD262 encoding the *Plasmodium yoelii*-chicken C4bp oligomerisation domain was expressed in the *E. coli* strain C41(DE3). The transformed cells were grown in LB medium at 37° C. to an OD600 of approximately 0.6, then expression was induced with IPTG to a final concentration of 0.5 mM, and the culture was grown for a further four hours at 37° C. at which point the cells were harvested by centrifugation.

Purification of AVD262 Fusion Protein

The protein AVD262 was purified from 1 liter of C41(DE3) cells. All of the fusion protein was found in the soluble fraction after the cells were lysed by sonication in a buffer containing 20 mM MES pH6.5, 5 mM EDTA and a cocktail of protease inhibitors (Roche). The supernatant after centrifugation was loaded on a HitrapS column.

Cationic Column (HiTrap S)

The column was equilibrated in 20 mM MES pH 6.5, 5 mM EDTA buffer (buffer A). The protein was eluted with a gradient of 10 column volumes from Buffer A to Buffer B (buffer A plus 1M NaCl). The HiTrapS fractions containing AVD262 were concentrated using a Millipore concentrator (cut-off 30 K) and then loaded on a gel filtration column, after denaturation overnight in a final volume of 10 mls in a buffer containing 50 mM Tris pH8 and 8M Urea.

First Gel Filtration Column (Superdex 200 26/60 Prep Grade) in the Presence of Urea A Superdex 200 26/60 column was equilibrated with 20 mM Tris buffer pH8, 150 mM NaCl and 8M urea, and the concentrated AVD262 protein from the HiTrapS fractions was loaded. The protein eluted in a volume of 186 mls, which was loaded onto a second Superdex 200 26/60 column, equilibrated in PBS.

Second Gel Filtration Column (Superdex 200 26/60 Prep Grade)

The concentrated AVD262 protein from the first Superdex 200 26/60 column was loaded. The protein, no longer denatured, eluted in a volume of 164 mls, as does the AVD108 protein.

Biophysical Characterisation

The oligomeric state of the AVD262 protein was checked by comparing its behaviour on an SDS-PAGE gel in the presence and absence of the reducing agent beta-mercaptoethanol (BME). As FIG. 4 shows, the AVD262 protein has an apparent size of approximately 140 kDa in the absence of BME (the intrasubunit disulphide bonds have formed following exposure to air), whereas in the presence of BME, it is reduced and runs with an apparent size of just over 20 kDa (as the disulphide bonds are unable to form in the reducing environment of the bacterial cytosol). In FIG. 4, each lane 1 contains 2.5 µg of purified protein, and each lane 2 contains 5 µg. It can clearly be seen that in the presence of BME (in the lanes labelled +βme) the protein migrates as a monomer with an apparent size of just over 20 kDa. In the absence of beta-mercaptoethanol (labelled –βme) the protein runs as a heptamer of approximately 140 kDa.

EXAMPLE 4

Immunisation of Mice

The purified AVD262 protein was used to immunise three BALB/c mice. No adjuvant was used, and the protein was in a buffered isotonic saline solution. Forty micrograms (2 nanomoles) of protein was used per injection. Each mouse was injected twice, subcutaneously, at four-weekly intervals (in other words, on days 0 and 29).

Three BALB/c mice were immunised with forty micrograms (also 2 nanomoles) of the AVD108 protein, which is the same as AVD262 but with the murine C4bp C-terminal 54 amino acids. Each mouse was injected twice, subcutaneously, on days 0 and 29.

Finally, three mice received 40 micrograms of AVD108 in Freund's adjuvant (complete for the first injection on day 0 followed by incomplete for the second injection on day 29). All mice were bled on day 43, and their antibody titres against the recombinant *Plasmodium yoelii* antigen were measured.

Mice which were injected with AVD108 alone had antibody titres of 25,600 or 51,200. Those which received AVD108 protein in Freund's adjuvant, had antibody titres of 102,400, as did those which received the AVD262 protein without adjuvant.

EXAMPLE 5

Immunisation of Rabbits

The purified AVD262 protein was used to immunise three New Zealand White (NZW) rabbits. The immunisation schedule was as follows: each rabbit received three injections at two-weekly intervals (in other words, on days 0, 14, and 28). Each injection was subcutaneous and contained 100 micrograms (or 4.5 nanomoles) of protein in a buffered isotonic saline solution without the addition of any known adjuvant.

In parallel, three NZW rabbits were immunised, according to the same schedule, with 20 nanomoles of AVD263 protein. The protein AVD263 is the same as AVD262 but the C4bp oligomerisation domain from rabbit C4bp replaces the C4bp oligomerisation from chicken. It has the amino acid sequence SEQ ID NO:21 as follows:

```
MRSHIASIALNNLNKSGLVGEGESKKILAKMLNMDGMDLLGVDPKHVCVD
TRDIPKNAGCFRDDNGTEEWRCLLGYKKGEGNTCVENNNPTCDINNGGCD
PTASCQNAESTENSKKIICTCKEPTPNAYYEGVFCSSSGSEVPEGCEQVQ
AGRRLMQCLADPYEVKMALEVYKLSLEIELLELQRDKARKSSVLRQL
```

Blood was drawn from each animal on day 35 and antibody titres against the recombinant *Plasmodium yoelii* antigen were measured by ELISA. The results were as follows: Rabbits which received the AVD262 protein had antibody titres of 25,600 while rabbits which received the AVD263 protein had antibody titres of 6,400. This is particularly striking as the amount of AVD262 protein used was less than the amount of AVD263 protein injected.

EXAMPLE 6

Immunisation of Chickens

The purified AVD262 protein was used to immunise three chickens. The immunisation schedule was as follows: each chicken received three injections at ten day intervals (in other words, on days 0, 10, and 20). Each injection was subcutaneous and contained 132 micrograms (or 6 nanomoles) of protein in a buffered isotonic saline solution without the addition of any known adjuvant.

In parallel, three chickens were immunised, according to the same schedule, with 6 nanomoles of AVD108 protein.

Blood was drawn from each animal on day 35 and antibody titres against the recombinant *Plasmodium yoelii* antigen were measured by ELISA. The results were as follows:

Chickens which received the AVD262 protein had antibody titres of 400 while chickens which received the AVD108 protein had antibody titres of 1,600.

EXAMPLE 7

Antibody Titres Against C4bp Oligomerisation Domains

Antibody titres were measured against both the murine and chicken C4bp oligomerisation domains in mice and chickens which were immunised with the AVD108 and AVD262 proteins. Mice which were immunised with the AVD108 protein had titres, measured by ELISA against the recombinant mouse C4bp oligomerisation domain, of 1600, but undetectable antibody titres against the recombinant AVD259 protein (no difference between pre-immune and day 43 titres). Mice which were immunised with the AVD262 protein had day 43 titres of 0 against the murine C4bp domain (i.e. there was no difference between pre-immune and day 43 sera) but these mice had day 43 titres of 12,800 against the AVD259 protein. This demonstrates that mice immunised with the non-mammalian C4bp domain fusion protein produces no antibodies against the endogenous murine C4bp domain, whereas the use of the murine C4bp oligomerisation domain for immunising mice does result in the induction of antibodies against the endogenous domain.

Chickens immunised with the same two proteins (AVD108 and AVD262), showed complementary results. Thus the chickens immunised with the AVD262 protein had antibody titres of 102,000 against the AVD259 protein, but 0 against the murine C4bp oligomerisation domain. But chickens immunised with the AVD108 protein had undetectable antibodies against the AVD259 protein, but antibody titres of 800 against the murine C4bp oligomerisation domain. No antibodies to the murine domain were detectable in pre-immune sera.

EXAMPLE 8

Isolation of Further Non-Mammalian C4bp Sequences

The nucleotide sequence encoding the chicken C4bp oligomerisation domain (shown in FIG. 1) was used to search the incomplete genomic DNA sequence of the zebrafinch (*Taeniopygia guttata*) using the discontinuous megablast program provided by NCBI (Worldwide Web Site:ncbi.nlm.nih.gov/blast/tracemb.shtml). Several trace sequences containing an identical 153 nucleotide sequence encoding the zebrafinch C4bp oligomerisation domain were found.

The zebrafinch C4bp oligomerisation domain has the nucleic acid sequence SEQ ID NO:22 as follows:

ATGAAAGAAGGTGATGGTGATGTGTGTCAAGAGGTTCATTACATTAAATC

GACCTTTGAATGTGGTGTGCCTGTAGAAGAAGTGAAAATTCTGCTGGAAA

TACAGAAACTGCTCCTGGAGATTAACAAACTAGAGATGGAGCTAGAAAAC

TAA

The zebrafinch C4bp oligomerisation domain has the amino acid sequence SEQ ID NO:23 as follows:

MKEGDGDVCQEVHYIKSTFECGVPVEEVKILLEIQKLLLEINKLEMELEN

An alignment of the zebrafinch C4bp oligomerisation domain with that of the chicken shows that only 48% (30/62) of the aligned amino acid residues are identical (highlighted in bold). Thus, the identification of homologous C4bp oligomerisation domains using the chicken DNA sequence is feasible even in raw DNA sequence databases. In the alignment below, the variant OD oligomerisation domain has the amino acid sequence of SEQ ID NO: 1 and the Zebrafinch oligomerisation domain has the amino acid sequence of SEQ ID NO: 23.

```
Variant OD
KKQGDADVCGEVAYIQSVVSDCHVPTEDVKTLLEIRKLFLEI

Zebrafinch
MKEGDGDVCQEVHYIKSTF ECGVPVEEVKILLEIQKLLLEI

Variant OD
QKLKVELQGLSKEFLEHILH*

Zebrafinch
NKLEMELEN*
```

EXAMPLE 9

Demonstration of the Activity of a Truncation Mutant of the Chicken C4bp Domain

The AVD262 protein described in example 3 was truncated by deleting the last seven C-terminal amino acids. The gene encoding the truncated version of the C4bp domain was amplified by PCR using the following oligonucleotide primers:

```
oAVD623:
                                         (SEQ ID NO: 24)
GGGGGAATTCCTTATTACTCCTTGCTCAGTCCTTGCAATTCC

T7F:
                                         (SEQ ID NO: 25)
TAATACGACTCACTATAGGG
```

The PCR product was digested by the restriction enzymes BamHI and EcoRI and re-cloned between the same sites of the pAVD262 vector thus creating the plasmid pAVD317.

The amino acid sequence of the protein AVD317 encoded by this construct is SEQ ID NO:26 as follows:

```
MRSHIASIAL  NNLNKSGLVG  EGESKKILAK  MLNMDGMDLL

GVDPKHVCVD  TRDIPKNAGC  FRDDNGTEEW  RCLLGYKKGE

GNTCVENNNP  TCDINNGGCD  PTASCQNAES  TENSKKIICT

CKEPTPNAYY  EGVFCSSSGS  KKQGDADVCG  EVAYIQSVVS

DCHVPTEDVK  TLLEIRKLFL  EIQKLKVELQ  GLSKE
```

The purification scheme described for the protein AVD262 was used to purify the AVD317 protein.

Mice were immunised using the same immunisation schedule as in example 4, namely three BALB/c mice were immunised without the addition of any adjuvant. The purified protein was in a buffered isotonic saline solution. Two nanomoles of protein were used per injection and each mouse was injected subcutaneously twice, with an interval of four weeks between the two injections (or in other words, on days 0 and 29). All mice were bled on day 43, and their antibody titres against the recombinant *Plasmodium yoelii* antigen were measured by ELISA.

Mice which were injected with AVD317 without any adjuvant had antibody titres of 104,000, showing that truncation has not diminished the biological activity of the chicken C4bp domain.

EXAMPLE 10

The Truncation Mutant of Example 9 Renders Insoluble Fusion Proteins Soluble

Proteins AVD290 and AVD291 were generated by fusing the peptide hormone GnRH (gonadotrophin releasing hormone) to either the long or short form of the domain, respectively. AVD290 was created by annealing the following two oligonucleotides:

```
oAVD607:
                                       (SEQ ID NO: 27)
5' TATGGAACATTGGAGCTATGGCCTGCGTCCGGGCG 3' oAVD608:
                                       (SEQ ID NO: 28)
5' GATCCGCCCGGACGCAGGCCATAGCTCCAATGTTCCA 3'
```

The annealed oligonucleotides were cloned between the NdeI and BamHI sites of the plasmid pAVD262.

The same two oligonucleotides were cloned between the NdeI and BamHI sites of pAVD317, to create the plasmid pAVD291.

The nucleotide sequence encoding the AVD290 fusion protein is SEQ ID NO:29 as follows:

ATGGAACATTGGAGCTATGGCCTGCGTCCGGGCGGATCCAAGAAGCAAGG

TGATGCTGATGTGTGCGGAGAGGTTGCTTATATTCAGAGCGTCGTCTCCG

ATTGCCACGTGCCTACAGAGGACGTGAAAACTCTGCTGGAAATACGAAAA

CTCTTCCTGGAGATTCAAAAACTGAAGGTGGAATTGCAAGGACTGAGCAA

GGAGTTCCTGGAGCACATTCTGCACTAA

The amino acid sequence of the fusion protein AVD290 encoded by this construct is SEQ ID NO:30 as follows:

```
MEHWSYGLRP GGSKKQGDAD VCGEVAYIQS VVSDCHVPTE

DVKTLLEIRK LFLEIQKLKV ELQGLSKEFL EHILH
```

The nucleotide sequence encoding the AVD291 fusion protein is SEQ ID NO:31 as follows:

ATGGAACATTGGAGCTATGGCCTGCGTCCGGGCGGATCCAAGAAGCAAGG

TGATGCTGATGTGTGCGGAGAGGTTGCTTATATTCAGAGCGTCGTCTCCG

ATTGCCACGTGCCTACAGAGGACGTGAAAACTCTGCTGGAAATACGAAAA

CTCTTCCTGGAGATTCAAAAACTGAAGGTGGAATTGCAAGGACTGAGCAA

GGAGTAA

The amino acid sequence of the fusion protein AVD291 encoded by this construct is SEQ ID NO:32 as follows:

```
MEHWSYGLRP GGSKKQGDAD VCGEVAYIQS VVSDCHVPTE

DVKTLLEIRK LFLEIQKLKV ELQGLSKE
```

The AVD290 protein was found to be >90% insoluble when expression was induced in the strain C41(DE3), using the following induction conditions: 0.5 mM IPTG was added when the OD600 was 0.5, and incubation was continued for three hours before the bacteria were harvested. The bacteria were lysed by disruption in an Emulsiflex apparatus. Under identical induction conditions, the AVD291 protein was soluble. The AVD291 protein even remained soluble after the extract of the lysed bacteria were heated at 75° C. for 15 minutes, which rendered most of the bacterial proteins insoluble.

These results illustrate that deletion of the last seven amino acids of the chicken domain can dramatically alter the solubility of a fusion protein.

As a result, purification was greatly simplified. The final steps of purification were performed by ion-exchange chromatography on DEAE in a buffer of 20 mM TrisHCl, pH7.0 (elution with a salt gradient, ten column volumes of 1M NaCl in the same buffer) and size-exclusion gel chromatography on a Superdex S75 26/60 column.

EXAMPLE 11

The C-Terminus of the Untruncated Chicken C4bp Domain Facilitates Protein Purification As discussed in previous examples, the proteins AVD262 and AVD317 differ only by the presence or absence of seven amino acids at the C-terminus. The AVD262 protein was purified on a nickel affinity chromatography column (Ni-NTA from GE) to which it binds, and from which it can be eluted by the addition of imidazole to the same buffer used for binding. The AVD317 protein did not bind to the column under identical conditions.

Bacteria expressing the AVD262 protein were lysed in a buffer containing only 10 mM TrisHCl pH7.0 and insoluble material was removed by centrifugation at 10,000 rpm in a Sorvall S34 rotor. To the new supernatant, NaCl was added to a final concentration of 300 mM and the solution was incubated with Ni-NTA for 1 hour at 4 C. The entire solution was then poured into a column and was washed first with a solution containing 50 mM NaPO4, 300 mM NaCl and 0.1% Triton X-100, pH 7.5 and then with the same buffer lacking Triton X-100. The AVD262 protein was eluted with a solution of 200 mM Imidazole, 150 mM NaCl pH 8.0.

EXAMPLE 12

Fusion to the Chicken C4bp Domain Renders Endogenous Antigens Highly Immunogenic The immunogenicity of GnRH when fused to the truncated domain (AVD291) was tested by immunising mice with the AVD291 protein.

Three BALB/c mice were immunised with 2 nanomoles of the AVD291 protein. Each mouse was injected twice, subcutaneously, on days 0 and 29. All mice were bled on day 43, and their antibody titres were measured against the recombinant protein obtained by fusing the GnRH antigen to the C-terminus of the glutathione S-transferase (GST) protein.

Two mice had a titre of antibodies of 5,120 while the third had an antibody titre of 10,240. In addition, three mice which received the AVD291 protein according to the same immunisation protocol, but in complete Freund's adjuvant for the first injection and in incomplete Freund's adjuvant for the second, had antibody titres of 5,120, 10,240 and 20,480, respectively.

This shows that fusion to the truncated chicken C4bp domain renders GnRH very immunogenic, and that the immunogenicity may be increased further by the addition of an adjuvant.

EXAMPLE 13

Mutation of Four Consecutive Amino Acids Does Not Diminish the Biological Activity of the Chicken C4bp Domain The plasmid pAVD317 was mutated using a site-directed mutagenesis kit containing Pfu Ultra from Stratagene and the following two oligonucleotides:

oAVD619:
(SEQ ID NO: 33)
CCGATTGCCACGTGCCTACAGCGGAACTGCGTACTCTGCTGGAAATACGA
AAACTC oAVD620:
(SEQ ID NO: 34)
GAGTTTTCGTATTTCCAGCAGAGTACGCAGTTCCGCTGTAGGCACGTGGC
AATCGG.

The nucleotide sequence encoding the AVD313 fusion protein is SEQ ID NO:35 as follows:

ATGAGATCTCACATTGCCTCTATTGCTTTGAACAACTTGAACAAGTCTGG

-continued
TTTGGTAGGAGAAGGTGAGTCTAAGAAGATTTTGGCTAAGATGCTGAACA

TGGACGGTATGGACTTGTTGGGTGTTGACCCTAAGCATGTTTGTGTTGAC

ACTAGAGACATTCCTAAGAACGCTGGATGTTTCAGAGACGACAACGGTAC

TGAAGAGTGGAGATGTTTGTTGGGTTACAAGAAGGGTGAGGGTAACACCT

GCGTTGAGAACAACAACCCTACTTGCGACATCAACAACGGTGGATGTGAC

CCAACCGCCTCTTGTCAAAACGCTGAATCTACCGAAAACTCCAAGAAGAT

TATTTGCACCTGTAAGGAACCAACCCCTAACGCCTACTACGAGGGTGTTT

TCTGTTCTTCTTCCGGATCCAAGAAGCAAGGTGATGCTGATGTGTGCGGA

GAGGTTGCTTATATTCAGAGCGTCGTCTCCGATTGCCACGTGCCTACAGC

GGAACTGCGTACTCTGCTGGAAATACGAAAACTCTTCCTGGAGATTCAAA

AACTGAAGGTGGAATTGCAAGGACTGAGCAAGGAGTAATAAGGAATTC

The amino acid sequence of the fusion protein AVD313 encoded by this construct is SEQ ID NO:36 as follows:

MRSHIASIAL NNLNKSGLVG EGESKKILAK MLNMDGMDLL
    GVDPKHVCVD TRDIPKNAGC FRDDNGTEEW RCLLGYKKGE
    GNTCVENNNP TCDINNGGCD PTASCQNAES TENSKKIICT
    CKEPTPNAYY EGVFCSSSGS KKQGDADVCG EVAYIQSVVS
    DCHVPT<u>AELR</u> TLLEIRKLFL EIQKLKVELQ GLSKE

The AVD313 protein was purified using the same buffers and columns as were used for the AVD262 protein.

Six BALB/c mice were immunised with 2 nanomoles of the AVD313 protein. Each mouse was injected twice, subcutaneously, on days 0 and 29. All mice were bled on day 43, and their antibody titres against the recombinant *Plasmodium yoelii* antigen were measured.

All mice which were injected with AVD313 alone had antibody titres of 204,000, showing that the truncation and mutation of the chicken C4bp domain has not diminished its biological activity.

The four amino acid alterations in AVD313 compared to AVD317 are underlined in the amino acid sequence of AVD313 as shown in SEQ ID NO:36. The modified chicken C4bp domain in the fusion protein AVD313 has less than 20% identity to the human C4bp domain, and thus is highly preferred for use in immunising humans, as the likelihood of eliciting antibodies that cross-react with human C4bp is very low.

EXAMPLE 14

The CRES Domain Shares the Biological Activity of the Chicken C4bp Domain

We examined whether the CRES domain (shown in FIG. 1) also increases the immunogenicity of antigens. The CRES domain in FIG. 1 has the following amino acid sequence:

SEQ ID NO 37:
PPNCKTFYVRKKIDQIKETFDCGLPLAELRTLLEVQKLYLEIQKLEKELGAKGGRWWP

The nucleotide sequence encoding the CRES domain was amplified from chicken genomic DNA using the following two oligonucleotide primers:

oAVD467:
(SEQ ID NO: 38)
GGGGGGATCCAAAACATTTTACGTACGCAAGAAGATTGATCAAATAAAGG oAVD468:
(SEQ ID NO: 39)
GGGGGAATTCTTATTACGGCCACCAGCGGCCTCCTTTGGC.

The PCR product was digested with the restriction enzymes BamHI and EcoRI and cloned between the same sites in the vector pAVD262 thus creating the plasmid pAVD314.

The nucleotide sequence encoding the AVD314 fusion protein is SEQ ID NO:40 as follows:

ATGAGATCTCACATTGCCTCTATTGCTTTGAACAACTTGAACAAGTCTGG

TTTGGTAGGAGAAGGTGAGTCTAAGAAGATTTTGGCTAAGATGCTGAACA

TGGACGGTATGGACTTGTTGGGTGTTGACCCTAAGCATGTTTGTGTTGAC

ACTAGAGACATTCCTAAGAACGCTGGATGTTTCAGAGACGACAACGGTAC

TGAAGAGTGGAGATGTTTGTTGGGTTACAAGAAGGGTGAGGGTAACACCT

GCGTTGAGAACAACAACCCTACTTGCGACATCAACAACGGTGGATGTGAC

CCAACCGCCTCTTGTCAAAACGCTGAATCTACCGAAAACTCCAAGAAGAT

TATTTGCACCTGTAAGGAACCAACCCCTAACGCCTACTACGAGGGTGTTT

TCTGTTCTTCTTCCGGATCCAAAACATTTTACGTACGCAAGAAGATTGAT

CAAATAAAGGAAACTTTTGATTGCGGATTGCCTCTGGCAGAACTGAGAAC

TCTGCTGGAAGTACAGAAGCTCTACCTGGAGATCCAGAAGCTGGAGAAGG

AGCTGGGAGCCAAAGGAGGCCGCTGGTGGCCGTAATAAGAATTC

The amino acid sequence of the fusion protein AVD314 encoded by this construct is SEQ ID NO:41 as follows:

MRSHIASIAL NNLNKSGLVG EGESKKILAK MLNMDGMDLL
    GVDPKHVCVD TRDIPKNAGC FRDDNGTEEW RCLLGYKKGE

```
GNTCVENNNP TCDINNGGCD PTASCQNAES TENSKKIICT

CKEPTPNAYY EGVFCSSSGS KTFYVRKKID QIKETFDCGL

PLAELRTLLE VQKLYLEIQK LEKELGAKGG RWWP
```

The AVD314 protein was purified using the same buffers and columns as were used for the AVD262 protein.

Three BALB/c mice were immunised with 2 nanomoles of the AVD314 protein. Each mouse was injected twice, subcutaneously, on days 0 and 29. All mice were bled on day 43, and their antibody titres against the recombinant *Plasmodium yoelii* antigen were measured.

All mice which were injected with AVD314 alone had antibody titres of 51,200, compared to titres of 204,000 with the AVD262 protein. This shows that the CRES domain, like the chicken C4bp domain, has biological activity and can significantly increase the immunogenicity of antigens.

The invention claimed is:

1. A method of providing an immune response to an antigen in a human or animal subject, said method comprising administering to said subject a product comprising said antigen coupled to a non-mammalian C4bp domain comprising the amino acid sequence set forth in SEQ ID NO:1 or a variant thereof wherein said variant has at least 45% amino acid sequence identity to SEQ ID NO:1.

2. The method of claim 1 wherein the C4bp domain consists of the residues 1-62 of SEQ ID NO:1.

3. The method of claim 1 wherein said variant is a fragment of at least 48 contiguous amino acids of SEQ ID NO:1.

4. The method of claim 1 wherein said variant comprises an N-terminal deletion of 1 to 8 amino acids of SEQ ID NO:1.

5. The method of claim 1 wherein said variant comprises a C-terminal deletion of 1 to 8 amino acids of SEQ ID NO:1.

6. The method of claim 5 wherein said variant has the amino acid sequence shown in SEQ ID NO:42.

7. The method of claim 1 wherein said variant comprises from 1 to 8 amino acid substitutions.

8. The method of claim 5 wherein said variant has the amino acid sequence shown in SEQ ID NO:43.

9. The method of claim 1 wherein the C4bp domain comprises the CRES (complement regulatory secretory protein of chicken) domain as shown in SEQ ID NO:37.

10. The method of claim 1 wherein said antigen is fused to the N- or C-terminal of said C4bp domain.

11. The method of claim 1 wherein said antigen is fused to the N- or C-terminal of said C4bp via a flexible linker.

12. The method of claim 1 wherein said antigen is endogenous in humans.

13. The method of claim 1 wherein the antigen is gonadotropin releasing hormone (GnRH).

14. The method of claim 1 wherein said product is administered together with a pharmaceutically acceptable diluent, carrier or adjuvant.

* * * * *

SEQUENCE LISTING

```
<160> NUMBER OF SEQ ID NOS: 44

<210> SEQ ID NO 1
<211> LENGTH: 62
<212> TYPE: PRT
<213> ORGANISM: Gallus gallus

<400> SEQUENCE: 1

Lys Lys Gln Gly Asp Ala Asp Val Cys Gly Glu Val Ala Tyr Ile Gln
1               5                   10                  15

Ser Val Val Ser Asp Cys His Val Pro Thr Glu Asp Val Lys Thr Leu
            20                  25                  30

Leu Glu Ile Arg Lys Leu Phe Leu Glu Ile Gln Lys Leu Lys Val Glu
        35                  40                  45

Leu Gln Gly Leu Ser Lys Glu Phe Leu Glu His Ile Leu His
    50                  55                  60

<210> SEQ ID NO 2
<211> LENGTH: 189
<212> TYPE: DNA
<213> ORGANISM: Gallus gallus
<220> FEATURE:
<221> NAME/KEY: CDS
<222> LOCATION: (1)..(189)

<400> SEQUENCE: 2 aag aag caa ggt gat gct gat gtg tgc gga gag gtt gct tat att cag       48
Lys Lys Gln Gly Asp Ala Asp Val Cys Gly Glu Val Ala Tyr Ile Gln
1               5                   10                  15 agc gtc gtc tcc gat tgc cac gtg cct aca gag gac gtg aaa act ctg       96
Ser Val Val Ser Asp Cys His Val Pro Thr Glu Asp Val Lys Thr Leu
            20                  25                  30 ctg gag ata cga aaa ctc ttc ctg gag att caa aaa ctg aag gtg gaa      144
Leu Glu Ile Arg Lys Leu Phe Leu Glu Ile Gln Lys Leu Lys Val Glu
        35                  40                  45 ttg caa gga ctg agc aag gag ttc ctg gag cac att ctg cac tga          189
Leu Gln Gly Leu Ser Lys Glu Phe Leu Glu His Ile Leu His
    50                  55                  60

<210> SEQ ID NO 3
<211> LENGTH: 57
<212> TYPE: PRT
<213> ORGANISM: Homo sapiens

<400> SEQUENCE: 3

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Ser Ala
        35                  40                  45
```

```
Arg Gln Ser Thr Leu Asp Lys Glu Leu
    50                  55
```

<210> SEQ ID NO 4

<400> SEQUENCE: 4

000

<210> SEQ ID NO 5
<211> LENGTH: 62
<212> TYPE: PRT
<213> ORGANISM: Artificial sequence
<220> FEATURE:
<223> OTHER INFORMATION: Synthetic sequence: Variant of C4bp domain

<400> SEQUENCE: 5

```
Lys Lys Gln Gly Asp Ala Asp Val Cys Gly Glu Val Ala Tyr Ile Gln
1               5                   10                  15

Ser Val Val Ser Asp Cys His Val Pro Thr Glu Asp Val Lys Thr Leu
                20                  25                  30

Leu Glu Val Arg Lys Leu Phe Leu Glu Ile Gln Lys Leu Lys Val Glu
            35                  40                  45

Leu Gln Gly Leu Ser Lys Glu Phe Leu Glu His Ile Leu His
    50                  55                  60
```

<210> SEQ ID NO 6
<211> LENGTH: 62
<212> TYPE: PRT
<213> ORGANISM: Artificial sequence
<220> FEATURE:
<223> OTHER INFORMATION: Synthetic sequence: Variant of C4bp domain

<400> SEQUENCE: 6

```
Lys Lys Gln Gly Asp Ala Asp Val Cys Gly Glu Val Ala Tyr Ile Gln
1               5                   10                  15

Ser Val Val Ser Asp Cys His Val Pro Thr Glu Asp Val Lys Met Leu
                20                  25                  30

Leu Glu Val Arg Lys Leu Phe Leu Glu Ile Gln Lys Leu Lys Val Glu
            35                  40                  45

Leu Gln Gly Leu Ser Lys Glu Phe Leu Glu His Ile Leu His
    50                  55                  60
```

<210> SEQ ID NO 7
<211> LENGTH: 62
<212> TYPE: PRT
<213> ORGANISM: Artificial sequence
<220> FEATURE:
<223> OTHER INFORMATION: Synthetic sequence: Variant of C4bp domain

<400> SEQUENCE: 7

```
Lys Lys Gln Gly Asp Ala Asp Val Cys Gly Glu Val Ile Tyr Ile Gln
1               5                   10                  15

Ser Val Val Ser Asp Cys His Val Pro Thr Glu Asp Val Arg Thr Leu
                20                  25                  30

Leu Glu Ile Arg Lys Leu Phe Leu Glu Ile Gln Lys Leu Lys Val Glu
            35                  40                  45

Leu Gln Gly Leu Ser Lys Glu Phe Leu Glu His Ile Leu His
    50                  55                  60
```

<210> SEQ ID NO 8
<211> LENGTH: 62

```
<212> TYPE: PRT
<213> ORGANISM: Artificial sequence
<220> FEATURE:
<223> OTHER INFORMATION: Synthetic sequence: Variant of C4bp domain

<400> SEQUENCE: 8

Lys Lys Gln Gly Asp Ala Asp Val Cys Gly Glu Val Ile Tyr Ile Gln
1               5                   10                  15

Ser Val Val Ser Asp Cys His Val Pro Thr Glu Asp Val Lys Thr Leu
            20                  25                  30

Leu Glu Ile Arg Lys Leu Phe Leu Glu Ile Gln Lys Leu Lys Val Glu
        35                  40                  45

Leu Asn Gly Leu Ser Lys Glu Phe Leu Glu His Ile Leu His
    50                  55                  60

<210> SEQ ID NO 9
<211> LENGTH: 62
<212> TYPE: PRT
<213> ORGANISM: Artificial sequence
<220> FEATURE:
<223> OTHER INFORMATION: Synthetic sequence: Variant of C4bp domain

<400> SEQUENCE: 9

Lys Lys Gln Gly Asp Ala Asp Val Cys Gly Glu Val Ile Tyr Ile Gln
1               5                   10                  15

Ser Val Val Ser Asp Cys His Val Pro Thr Glu Asp Val Lys Met Leu
            20                  25                  30

Leu Glu Ile Arg Lys Leu Phe Leu Glu Ile Gln Lys Leu Lys Val Glu
        35                  40                  45

Leu Asn Gly Leu Ser Lys Glu Phe Leu Glu His Ile Leu His
    50                  55                  60

<210> SEQ ID NO 10
<211> LENGTH: 62
<212> TYPE: PRT
<213> ORGANISM: Artificial sequence
<220> FEATURE:
<223> OTHER INFORMATION: Synthetic sequence: Variant of C4bp domain

<400> SEQUENCE: 10

Lys Lys Gln Gly Asp Ala Asp Val Cys Gly Glu Val Ile Tyr Ile Gln
1               5                   10                  15

Ser Val Val Ser Asp Cys Leu Pro Asn Thr Glu Asp Val Lys Thr Leu
            20                  25                  30

Leu Glu Val Arg Lys Leu Phe Leu Glu Ile Gln Lys Leu Lys Val Glu
        35                  40                  45

Leu Gln Gly Leu Ser Lys Glu Phe Leu Glu His Ile Leu His
    50                  55                  60

<210> SEQ ID NO 11
<211> LENGTH: 54
<212> TYPE: PRT
<213> ORGANISM: Artificial sequence
<220> FEATURE:
<223> OTHER INFORMATION: Synthetic sequence: Variant of C4bp domain

<400> SEQUENCE: 11

Asp Ala Asp Val Cys Gly Glu Val Ala Tyr Ile Gln Ser Val Val Ser
1               5                   10                  15

Asp Cys His Val Pro Thr Glu Asp Val Lys Thr Leu Leu Glu Ile Arg
            20                  25                  30

Lys Leu Phe Leu Glu Ile Gln Lys Leu Lys Val Glu Leu Gln Gly Leu
```

```
            35                  40                  45

Ser Lys Glu Phe Leu Glu
     50

<210> SEQ ID NO 12
<211> LENGTH: 51
<212> TYPE: PRT
<213> ORGANISM: Artificial sequence
<220> FEATURE:
<223> OTHER INFORMATION: Synthetic sequence: Variant of C4bp domain

<400> SEQUENCE: 12

Ala Asp Val Cys Gly Glu Val Ala Tyr Ile Gln Ser Val Val Ser Asp
1               5                  10                  15

Cys His Val Pro Thr Glu Asp Val Lys Thr Leu Leu Glu Ile Arg Lys
            20                  25                  30

Leu Phe Leu Glu Ile Gln Lys Leu Lys Val Glu Leu Gln Gly Leu Ser
        35                  40                  45

Lys Glu Phe
     50

<210> SEQ ID NO 13
<211> LENGTH: 51
<212> TYPE: PRT
<213> ORGANISM: Artificial sequence
<220> FEATURE:
<223> OTHER INFORMATION: Synthetic sequence: Variant of C4bp domain

<400> SEQUENCE: 13

Ala Asp Val Cys Gly Glu Val Ile Tyr Ile Gln Ser Val Val Ser Asp
1               5                  10                  15

Cys His Val Pro Thr Glu Asp Val Lys Thr Leu Leu Glu Val Arg Lys
            20                  25                  30

Leu Phe Leu Glu Ile Gln Lys Leu Lys Val Glu Leu Gln Gly Leu Ser
        35                  40                  45

Lys Glu Phe
     50

<210> SEQ ID NO 14
<211> LENGTH: 48
<212> TYPE: PRT
<213> ORGANISM: Artificial sequence
<220> FEATURE:
<223> OTHER INFORMATION: Synthetic sequence: Variant of C4bp domain

<400> SEQUENCE: 14

Ala Asp Val Cys Gly Glu Val Ala Tyr Ile Gln Ser Val Val Ser Asp
1               5                  10                  15

Cys His Val Pro Thr Glu Asp Val Lys Thr Leu Leu Glu Ile Arg Lys
            20                  25                  30

Leu Phe Leu Glu Ile Gln Lys Leu Lys Val Glu Leu Asn Gly Leu Ser
        35                  40                  45

<210> SEQ ID NO 15
<211> LENGTH: 39
<212> TYPE: DNA
<213> ORGANISM: Artificial sequence
<220> FEATURE:
<223> OTHER INFORMATION: Synthetic sequence: Oligonucleotide primer
      oAVD469

<400> SEQUENCE: 15 gggggggatcc aagaagcaag gtgatgctga tgtgtgcgg                           39
```

<210> SEQ ID NO 16
<211> LENGTH: 40
<212> TYPE: DNA
<213> ORGANISM: Artificial sequence
<220> FEATURE:
<223> OTHER INFORMATION: Synthetic sequence: Oligonucleotide primer oAVD470

<400> SEQUENCE: 16
gggggaattc ttattagtgc agaatgtgct ccaggaactc                               40

<210> SEQ ID NO 17
<211> LENGTH: 78
<212> TYPE: PRT
<213> ORGANISM: Gallus gallus

<400> SEQUENCE: 17

Met Ala Leu Lys Lys His His Glu Asn Glu Ile Ser His His Gly Ser
1               5                   10                  15

Lys Lys Gln Gly Asp Ala Asp Val Cys Gly Glu Val Ala Tyr Ile Gln
            20                  25                  30

Ser Val Val Ser Asp Cys His Val Pro Thr Glu Asp Val Lys Thr Leu
        35                  40                  45

Leu Glu Ile Arg Lys Leu Phe Leu Glu Ile Gln Lys Leu Lys Val Glu
    50                  55                  60

Leu Gln Gly Leu Ser Lys Glu Phe Leu Glu His Ile Leu His
65                  70                  75

<210> SEQ ID NO 18
<211> LENGTH: 237
<212> TYPE: DNA
<213> ORGANISM: Gallus gallus

<400> SEQUENCE: 18
atggccttga agaaacacca tgaaaatgag atctctcatc atggatccaa gaagcaaggt        60
gatgctgatg tgtgcggaga ggttgcttat attcagagcg tcgtctccga ttgccacgtg       120
cctacagagg acgtgaaaac tctgctggaa atacgaaaac tcttcctgga gattcaaaaa       180
ctgaaggtgg aattgcaagg actgagcaag gagttcctgg agcacattct gcactaa         237

<210> SEQ ID NO 19
<211> LENGTH: 609
<212> TYPE: DNA
<213> ORGANISM: Artificial sequence
<220> FEATURE:
<223> OTHER INFORMATION: Synthetic sequence: Nucleotide sequence encoding the AVD262 fusion protein

<400> SEQUENCE: 19
atgagatctc acattgcctc tattgctttg aacaacttga acaagtctgg tttggtagga        60
gaaggtgagt ctaagaagat tttggctaag atgctgaaca tggacggtat ggacttgttg       120
ggtgttgacc ctaagcatgt ttgtgttgac actagagaca ttcctaagaa cgctggatgt       180
ttcagagacg acaacggtac tgaagagtgg agatgtttgt tgggttacaa gaagggtgag       240
ggtaacacct gcgttgagaa caacaaccct acttgcgaca tcaacaacgg tggatgtgac       300
ccaaccgcct cttgtcaaaa cgctgaatct accgaaaact ccagaagat tatttgcacc       360 tgtaaggaac caaccccctaa cgcctactac gagggtgttt tctgttcttc ttccggatcc       420
aagaagcaag gtgatgctga tgtgtgcgga gaggttgctt atattcagag cgtcgtctcc       480

```
gattgccacg tgcctacaga ggacgtgaaa actctgctgg aaatacgaaa actcttcctg    540
gagattcaaa aactgaaggt ggaattgcaa ggactgagca aggagttcct ggagcacatt    600
ctgcactaa                                                            609
```

<210> SEQ ID NO 20
<211> LENGTH: 202
<212> TYPE: PRT
<213> ORGANISM: Artificial sequence
<220> FEATURE:
<223> OTHER INFORMATION: Synthetic sequence: AVD262 fusion protein
      encoded by SEQ ID NO: 19

<400> SEQUENCE: 20

```
Met Arg Ser His Ile Ala Ser Ile Ala Leu Asn Asn Leu Asn Lys Ser
1               5                   10                  15

Gly Leu Val Gly Glu Gly Glu Ser Lys Lys Ile Leu Ala Lys Met Leu
            20                  25                  30

Asn Met Asp Gly Met Asp Leu Leu Gly Val Asp Pro Lys His Val Cys
        35                  40                  45

Val Asp Thr Arg Asp Ile Pro Lys Asn Ala Gly Cys Phe Arg Asp Asp
    50                  55                  60

Asn Gly Thr Glu Glu Trp Arg Cys Leu Leu Gly Tyr Lys Lys Gly Glu
65                  70                  75                  80

Gly Asn Thr Cys Val Glu Asn Asn Pro Thr Cys Asp Ile Asn Asn
                85                  90                  95

Gly Gly Cys Asp Pro Thr Ala Ser Cys Gln Asn Ala Glu Ser Thr Glu
            100                 105                 110

Asn Ser Lys Lys Ile Ile Cys Thr Cys Lys Glu Pro Thr Pro Asn Ala
        115                 120                 125

Tyr Tyr Glu Gly Val Phe Cys Ser Ser Ser Gly Ser Lys Lys Gln Gly
    130                 135                 140

Asp Ala Asp Val Cys Gly Glu Val Ala Tyr Ile Gln Ser Val Val Ser
145                 150                 155                 160

Asp Cys His Val Pro Thr Glu Asp Val Lys Thr Leu Leu Glu Ile Arg
                165                 170                 175

Lys Leu Phe Leu Glu Ile Gln Lys Leu Lys Val Glu Leu Gln Gly Leu
            180                 185                 190

Ser Lys Glu Phe Leu Glu His Ile Leu His
        195                 200
```

<210> SEQ ID NO 21
<211> LENGTH: 197
<212> TYPE: PRT
<213> ORGANISM: Artificial sequence
<220> FEATURE:
<223> OTHER INFORMATION: Synthetic sequence: AVD263 protein

<400> SEQUENCE: 21

```
Met Arg Ser His Ile Ala Ser Ile Ala Leu Asn Asn Leu Asn Lys Ser
1               5                   10                  15

Gly Leu Val Gly Glu Gly Glu Ser Lys Lys Ile Leu Ala Lys Met Leu
            20                  25                  30

Asn Met Asp Gly Met Asp Leu Leu Gly Val Asp Pro Lys His Val Cys
        35                  40                  45

Val Asp Thr Arg Asp Ile Pro Lys Asn Ala Gly Cys Phe Arg Asp Asp
    50                  55                  60

Asn Gly Thr Glu Glu Trp Arg Cys Leu Leu Gly Tyr Lys Lys Gly Glu
65                  70                  75                  80
```

Gly Asn Thr Cys Val Glu Asn Asn Pro Thr Cys Asp Ile Asn Asn
                85                  90                  95

Gly Gly Cys Asp Pro Thr Ala Ser Cys Gln Asn Ala Glu Ser Thr Glu
            100                 105                 110

Asn Ser Lys Lys Ile Ile Cys Thr Cys Lys Glu Pro Thr Pro Asn Ala
            115                 120                 125

Tyr Tyr Glu Gly Val Phe Cys Ser Ser Ser Gly Ser Glu Val Pro Glu
            130                 135                 140

Gly Cys Glu Gln Val Gln Ala Gly Arg Arg Leu Met Gln Cys Leu Ala
145                 150                 155                 160

Asp Pro Tyr Glu Val Lys Met Ala Leu Glu Val Tyr Lys Leu Ser Leu
                165                 170                 175

Glu Ile Glu Leu Leu Glu Leu Gln Arg Asp Lys Ala Arg Lys Ser Ser
            180                 185                 190

Val Leu Arg Gln Leu
        195

<210> SEQ ID NO 22
<211> LENGTH: 153
<212> TYPE: DNA
<213> ORGANISM: Taeniopygia guttata

<400> SEQUENCE: 22
atgaaagaag gtgatggtga tgtgtgtcaa gaggttcatt acattaaatc gacctttgaa     60
tgtggtgtgc ctgtagaaga agtgaaaatt ctgctggaaa tacagaaact gctcctggag    120
attaacaaac tagagatgga gctagaaaac taa                                 153

<210> SEQ ID NO 23
<211> LENGTH: 50
<212> TYPE: PRT
<213> ORGANISM: Taeniopygia guttata

<400> SEQUENCE: 23

Met Lys Glu Gly Asp Gly Asp Val Cys Gln Glu Val His Tyr Ile Lys
1               5                   10                  15

Ser Thr Phe Glu Cys Gly Val Pro Val Glu Glu Val Lys Ile Leu Leu
            20                  25                  30

Glu Ile Gln Lys Leu Leu Leu Glu Ile Asn Lys Leu Glu Met Glu Leu
        35                  40                  45

Glu Asn
    50

<210> SEQ ID NO 24
<211> LENGTH: 42
<212> TYPE: DNA
<213> ORGANISM: Artificial sequence
<220> FEATURE:
<223> OTHER INFORMATION: Synthetic sequence: Oligonucleotide primer
      oAVD623

<400> SEQUENCE: 24
gggggaattc cttattactc cttgctcagt ccttgcaatt cc                        42

<210> SEQ ID NO 25
<211> LENGTH: 20
<212> TYPE: DNA
<213> ORGANISM: Artificial sequence
<220> FEATURE:
<223> OTHER INFORMATION: Synthetic sequence: Oligonucleotide primer T7F

<400> SEQUENCE: 25
taatacgact cactataggg                                                        20

<210> SEQ ID NO 26
<211> LENGTH: 195
<212> TYPE: PRT
<213> ORGANISM: Artificial sequence
<220> FEATURE:
<223> OTHER INFORMATION: Synthetic sequence: AVD317 protein

<400> SEQUENCE: 26

Met Arg Ser His Ile Ala Ser Ile Ala Leu Asn Asn Leu Asn Lys Ser
1               5                   10                  15

Gly Leu Val Gly Glu Gly Glu Ser Lys Lys Ile Leu Ala Lys Met Leu
            20                  25                  30

Asn Met Asp Gly Met Asp Leu Leu Gly Val Asp Pro Lys His Val Cys
        35                  40                  45

Val Asp Thr Arg Asp Ile Pro Lys Asn Ala Gly Cys Phe Arg Asp Asp
    50                  55                  60

Asn Gly Thr Glu Glu Trp Arg Cys Leu Leu Gly Tyr Lys Lys Gly Glu
65                  70                  75                  80

Gly Asn Thr Cys Val Glu Asn Asn Pro Thr Cys Asp Ile Asn Asn
                85                  90                  95

Gly Gly Cys Asp Pro Thr Ala Ser Cys Gln Asn Ala Glu Ser Thr Glu
            100                 105                 110

Asn Ser Lys Lys Ile Ile Cys Thr Cys Lys Glu Pro Thr Pro Asn Ala
        115                 120                 125

Tyr Tyr Glu Gly Val Phe Cys Ser Ser Ser Gly Ser Lys Lys Gln Gly
    130                 135                 140

Asp Ala Asp Val Cys Gly Glu Val Ala Tyr Ile Gln Ser Val Val Ser
145                 150                 155                 160

Asp Cys His Val Pro Thr Glu Asp Val Lys Thr Leu Leu Glu Ile Arg
                165                 170                 175

Lys Leu Phe Leu Glu Ile Gln Lys Leu Lys Val Glu Leu Gln Gly Leu
            180                 185                 190

Ser Lys Glu
    195

<210> SEQ ID NO 27
<211> LENGTH: 35
<212> TYPE: DNA
<213> ORGANISM: Artificial sequence
<220> FEATURE:
<223> OTHER INFORMATION: Synthetic sequence: Oligonucleotide oAVD607

<400> SEQUENCE: 27
tatggaacat tggagctatg gcctgcgtcc gggcg                                       35

<210> SEQ ID NO 28
<211> LENGTH: 37
<212> TYPE: DNA
<213> ORGANISM: Artificial sequence
<220> FEATURE:
<223> OTHER INFORMATION: Synthetic sequence: Oligonucleotide oAVD608

<400> SEQUENCE: 28
gatccgcccg gacgcaggcc atagctccaa tgttcca                                     37

<210> SEQ ID NO 29
<211> LENGTH: 228

```
<212> TYPE: DNA
<213> ORGANISM: Artificial sequence
<220> FEATURE:
<223> OTHER INFORMATION: Synthetic sequence: Nucleotide sequence
      encoding the AVD290 fusion protein

<400> SEQUENCE: 29
atggaacatt ggagctatgg cctgcgtccg gcggatcca agaagcaagg tgatgctgat      60
gtgtgcggag aggttgctta tattcagagc gtcgtctccg attgccacgt gcctacagag     120
gacgtgaaaa ctctgctgga aatacgaaaa ctcttcctgg agattcaaaa actgaaggtg     180
gaattgcaag gactgagcaa ggagttcctg agcacattc tgcactaa                   228

<210> SEQ ID NO 30
<211> LENGTH: 75
<212> TYPE: PRT
<213> ORGANISM: Artificial sequence
<220> FEATURE:
<223> OTHER INFORMATION: Synthetic sequence: AVD290 fusion protein
      encoded by SEQ ID NO: 29

<400> SEQUENCE: 30

Met Glu His Trp Ser Tyr Gly Leu Arg Pro Gly Gly Ser Lys Lys Gln
1               5                   10                  15

Gly Asp Ala Asp Val Cys Gly Glu Val Ala Tyr Ile Gln Ser Val Val
            20                  25                  30

Ser Asp Cys His Val Pro Thr Glu Asp Val Lys Thr Leu Leu Glu Ile
        35                  40                  45

Arg Lys Leu Phe Leu Glu Ile Gln Lys Leu Lys Val Glu Leu Gln Gly
    50                  55                  60

Leu Ser Lys Glu Phe Leu Glu His Ile Leu His
65                  70                  75

<210> SEQ ID NO 31
<211> LENGTH: 207
<212> TYPE: DNA
<213> ORGANISM: Artificial sequence
<220> FEATURE:
<223> OTHER INFORMATION: Synthetic sequence: Nucleotide sequence
      encoding the AVD291 fusion protein

<400> SEQUENCE: 31
atggaacatt ggagctatgg cctgcgtccg gcggatcca agaagcaagg tgatgctgat      60
gtgtgcggag aggttgctta tattcagagc gtcgtctccg attgccacgt gcctacagag     120
gacgtgaaaa ctctgctgga aatacgaaaa ctcttcctgg agattcaaaa actgaaggtg     180
gaattgcaag gactgagcaa ggagtaa                                         207

<210> SEQ ID NO 32
<211> LENGTH: 68
<212> TYPE: PRT
<213> ORGANISM: Artificial sequence
<220> FEATURE:
<223> OTHER INFORMATION: Synthetic sequence: AVD291 fusion protein
      encoded by SEQ ID NO: 31

<400> SEQUENCE: 32

Met Glu His Trp Ser Tyr Gly Leu Arg Pro Gly Gly Ser Lys Lys Gln
1               5                   10                  15

Gly Asp Ala Asp Val Cys Gly Glu Val Ala Tyr Ile Gln Ser Val Val
            20                  25                  30

Ser Asp Cys His Val Pro Thr Glu Asp Val Lys Thr Leu Leu Glu Ile
        35                  40                  45
```

Arg Lys Leu Phe Leu Glu Ile Gln Lys Leu Lys Val Glu Leu Gln Gly
    50                  55                  60

Leu Ser Lys Glu
65

<210> SEQ ID NO 33
<211> LENGTH: 56
<212> TYPE: DNA
<213> ORGANISM: Artificial sequence
<220> FEATURE:
<223> OTHER INFORMATION: Synthetic sequence: Oligonucleotide oAVD619

<400> SEQUENCE: 33
ccgattgcca cgtgcctaca gcggaactgc gtactctgct ggaaatacga aaactc        56

<210> SEQ ID NO 34
<211> LENGTH: 56
<212> TYPE: DNA
<213> ORGANISM: Artificial sequence
<220> FEATURE:
<223> OTHER INFORMATION: Synthetic sequence: Oligonucleotide oAVD620

<400> SEQUENCE: 34
gagttttcgt atttccagca gagtacgcag ttccgctgta ggcacgtggc aatcgg        56

<210> SEQ ID NO 35
<211> LENGTH: 598
<212> TYPE: DNA
<213> ORGANISM: Artificial sequence
<220> FEATURE:
<223> OTHER INFORMATION: Synthetic sequence: Nucleotide sequence
      encoding the AVD313 fusion protein

<400> SEQUENCE: 35
atgagatctc acattgcctc tattgctttg aacaacttga acaagtctgg tttggtagga        60
gaaggtgagt ctaagaagat tttggctaag atgctgaaca tggacggtat ggacttgttg       120
ggtgttgacc ctaagcatgt ttgtgttgac actagagaca ttcctaagaa cgctggatgt       180
ttcagagacg acaacggtac tgaagagtgg agatgtttgt tgggttacaa gaagggtgag       240
ggtaacacct gcgttgagaa caacaaccct acttgcgaca tcaacaacgg tggatgtgac       300
ccaaccgcct cttgtcaaaa cgctgaatct accgaaaact ccaagaagat tatttgcacc       360
tgtaaggaac aacccctaa cgcctactac gagggtgttt tctgttcttc ttccggatcc        420
aagaagcaag gtgatgctga tgtgtgcgga gaggttgctt atattcagag cgtcgtctcc       480
gattgccacg tgcctacagc ggaactgcgt actctgctgg aaatacgaaa actcttcctg       540
gagattcaaa aactgaaggt ggaattgcaa ggactgagca ggagtaata aggaattc        598

<210> SEQ ID NO 36
<211> LENGTH: 195
<212> TYPE: PRT
<213> ORGANISM: Artificial sequence
<220> FEATURE:
<223> OTHER INFORMATION: Synthetic sequence: AVD313 fusion protein
      encoded by SEQ ID NO: 35

<400> SEQUENCE: 36

Met Arg Ser His Ile Ala Ser Ile Ala Leu Asn Asn Leu Asn Lys Ser
1               5                   10                  15

Gly Leu Val Gly Glu Gly Glu Ser Lys Lys Ile Leu Ala Lys Met Leu
                20                  25                  30

Asn Met Asp Gly Met Asp Leu Leu Gly Val Asp Pro Lys His Val Cys

```
                 35                  40                  45

Val Asp Thr Arg Asp Ile Pro Lys Asn Ala Gly Cys Phe Arg Asp Asp
 50                  55                  60

Asn Gly Thr Glu Glu Trp Arg Cys Leu Leu Gly Tyr Lys Lys Gly Glu
 65                  70                  75                  80

Gly Asn Thr Cys Val Glu Asn Asn Pro Thr Cys Asp Ile Asn Asn
                 85                  90                  95

Gly Gly Cys Asp Pro Thr Ala Ser Cys Gln Asn Ala Glu Ser Thr Glu
                100                 105                 110

Asn Ser Lys Lys Ile Ile Cys Thr Cys Lys Glu Pro Thr Pro Asn Ala
                115                 120                 125

Tyr Tyr Glu Gly Val Phe Cys Ser Ser Ser Gly Ser Lys Lys Gln Gly
                130                 135                 140

Asp Ala Asp Val Cys Gly Glu Val Ala Tyr Ile Gln Ser Val Val Ser
145                 150                 155                 160

Asp Cys His Val Pro Thr Ala Glu Leu Arg Thr Leu Leu Glu Ile Arg
                165                 170                 175

Lys Leu Phe Leu Glu Ile Gln Lys Leu Lys Val Glu Leu Gln Gly Leu
                180                 185                 190

Ser Lys Glu
    195

<210> SEQ ID NO 37
<211> LENGTH: 58
<212> TYPE: PRT
<213> ORGANISM: Gallus gallus

<400> SEQUENCE: 37

Pro Pro Asn Cys Lys Thr Phe Tyr Val Arg Lys Lys Ile Asp Gln Ile
 1               5                  10                  15

Lys Glu Thr Phe Asp Cys Gly Leu Pro Leu Ala Glu Leu Arg Thr Leu
                 20                  25                  30

Leu Glu Val Gln Lys Leu Tyr Leu Glu Ile Gln Lys Leu Glu Lys Glu
                 35                  40                  45

Leu Gly Ala Lys Gly Gly Arg Trp Trp Pro
 50                  55

<210> SEQ ID NO 38
<211> LENGTH: 50
<212> TYPE: DNA
<213> ORGANISM: Artificial sequence
<220> FEATURE:
<223> OTHER INFORMATION: Synthetic sequence: Oligonucleotide primer
      oAVD467

<400> SEQUENCE: 38 gggggatcc aaaacatttt acgtacgcaa gaagattgat caaataaagg            50

<210> SEQ ID NO 39
<211> LENGTH: 40
<212> TYPE: DNA
<213> ORGANISM: Artificial sequence
<220> FEATURE:
<223> OTHER INFORMATION: Synthetic sequence: Oligonucleotide primer
      oAVD468

<400> SEQUENCE: 39
gggggaattc ttattacggc caccagcggc ctcctttggc                      40

<210> SEQ ID NO 40
```

```
<211> LENGTH: 594
<212> TYPE: DNA
<213> ORGANISM: Artificial sequence
<220> FEATURE:
<223> OTHER INFORMATION: Synthetic sequence: Nucleotide sequence
      encoding the AVD314 fusion protein

<400> SEQUENCE: 40
atgagatctc acattgcctc tattgctttg aacaacttga acaagtctgg tttggtagga        60
gaaggtgagt ctaagaagat tttggctaag atgctgaaca tggacggtat ggacttgttg       120
ggtgttgacc ctaagcatgt ttgtgttgac actagagaca ttcctaagaa cgctggatgt       180
ttcagagacg acaacggtac tgaagagtgg agatgtttgt tgggttacaa gaagggtgag       240
ggtaacacct gcgttgagaa caacaaccct acttgcgaca tcaacaacgg tggatgtgac       300
ccaaccgcct cttgtcaaaa cgctgaatct accgaaaact ccaagaagat tatttgcacc       360
tgtaaggaac aaccccctaa cgcctactac gagggtgttt tctgttcttc ttccggatcc       420
aaaacatttt acgtacgcaa gaagattgat caaataaagg aaactttga ttgcggattg        480 cctctggcag aactgagaac tctgctggaa gtacagaagc tctacctgga gatccagaag       540
ctggagaagg agctgggagc caaaggaggc cgctggtggc cgtaataaga attc             594

<210> SEQ ID NO 41
<211> LENGTH: 194
<212> TYPE: PRT
<213> ORGANISM: Artificial sequence
<220> FEATURE:
<223> OTHER INFORMATION: Synthetic sequence: AVD314 fusion protein
      encoded by SEQ ID NO: 40

<400> SEQUENCE: 41

Met Arg Ser His Ile Ala Ser Ile Ala Leu Asn Asn Leu Asn Lys Ser
1               5                   10                  15

Gly Leu Val Gly Glu Gly Glu Ser Lys Lys Ile Leu Ala Lys Met Leu
            20                  25                  30

Asn Met Asp Gly Met Asp Leu Leu Gly Val Asp Pro Lys His Val Cys
        35                  40                  45

Val Asp Thr Arg Asp Ile Pro Lys Asn Ala Gly Cys Phe Arg Asp Asp
    50                  55                  60

Asn Gly Thr Glu Glu Trp Arg Cys Leu Leu Gly Tyr Lys Lys Gly Glu
65                  70                  75                  80

Gly Asn Thr Cys Val Glu Asn Asn Asn Pro Thr Cys Asp Ile Asn Asn
                85                  90                  95

Gly Gly Cys Asp Pro Thr Ala Ser Cys Gln Asn Ala Glu Ser Thr Glu
            100                 105                 110

Asn Ser Lys Lys Ile Ile Cys Thr Cys Lys Glu Pro Thr Pro Asn Ala
        115                 120                 125

Tyr Tyr Glu Gly Val Phe Cys Ser Ser Ser Gly Ser Lys Thr Phe Tyr
    130                 135                 140

Val Arg Lys Lys Ile Asp Gln Ile Lys Glu Thr Phe Asp Cys Gly Leu
145                 150                 155                 160

Pro Leu Ala Glu Leu Arg Thr Leu Leu Glu Val Gln Lys Leu Tyr Leu
                165                 170                 175

Glu Ile Gln Lys Leu Glu Lys Leu Gly Ala Lys Gly Gly Arg Trp
            180                 185                 190

Trp Pro

<210> SEQ ID NO 42
```

-continued

```
<211> LENGTH: 55
<212> TYPE: PRT
<213> ORGANISM: Artificial sequence
<220> FEATURE:
<223> OTHER INFORMATION: Synthetic sequence: Variant of C4bp domain

<400> SEQUENCE: 42

Lys Lys Gln Gly Asp Ala Asp Val Cys Gly Glu Val Ala Tyr Ile Gln
1               5                   10                  15

Ser Val Val Ser Asp Cys His Val Pro Thr Glu Asp Val Lys Thr Leu
            20                  25                  30

Leu Glu Ile Arg Lys Leu Phe Leu Glu Ile Gln Lys Leu Lys Val Glu
        35                  40                  45

Leu Gln Gly Leu Ser Lys Glu
    50                  55

<210> SEQ ID NO 43
<211> LENGTH: 55
<212> TYPE: PRT
<213> ORGANISM: Artificial sequence
<220> FEATURE:
<223> OTHER INFORMATION: Synthetic sequence: Variant of C4bp domain

<400> SEQUENCE: 43

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Leu Gln Gly Leu Ser Lys Glu
    50                  55

<210> SEQ ID NO 44
<211> LENGTH: 7
<212> TYPE: PRT
<213> ORGANISM: Gallus gallus

<400> SEQUENCE: 44

Phe Leu Glu His Ile Leu His
1               5
```